(12) United States Patent
Loiseau et al.

(10) Patent No.: US 8,163,706 B2
(45) Date of Patent: *Apr. 24, 2012

(54) **METHOD FOR PREPARING A *CENTELLA ASIATICA* EXTRACT RICH IN MADECASSOSIDE AND IN TERMINOLOSIDE**

(75) Inventors: Alain Loiseau, Bouillon (FR); Gérard Sene, Paris (FR); Eric Theron, Montardon (FR)

(73) Assignee: Bayer Consumer Care AG (CH)

( * ) Notice: Subject to any disclaimer, the term of this patent is extended or adjusted under 35 U.S.C. 154(b) by 348 days.

This patent is subject to a terminal disclaimer.

(21) Appl. No.: 12/009,696

(22) Filed: Jan. 22, 2008

(65) Prior Publication Data

US 2008/0118581 A1 May 22, 2008

Related U.S. Application Data

(63) Continuation of application No. 10/537,936, filed as application No. PCT/FR03/03651 on Dec. 10, 2003, now Pat. No. 7,402,669.

(51) Int. Cl.
*A01N 45/00* (2006.01)
(52) U.S. Cl. .......................................................... 514/26
(58) Field of Classification Search .................. None
See application file for complete search history.

(56) References Cited

U.S. PATENT DOCUMENTS

| 6,417,349 B1 | 7/2002 | Kim et al. |
| 2002/0098213 A1 | 7/2002 | Bonte et al. |

FOREIGN PATENT DOCUMENTS

| EP | 0 867 447 B1 | 9/1998 |
| WO | 97/39734 A1 | 10/1997 |
| WO | WO-01/19365 A1 | 3/2001 |

OTHER PUBLICATIONS

Database Bois 'online Biosciences Information Service, Philadelphia, PA, US, Collins D J, et al., "Triterpene Acids From Some Papua New Guinea Terminalia Species" XP002251030, 1992.
Database WPI, Section Ch, Week 199239 Derwent Publications Ltd., London, GB; Class B04 AN 1992-321 31 0 XP002251031.
Matsuda et al., "Medicinal Foodstuffs.XXVII[1]) Saponin Constituents of Gotu Kola (2): Structures of New Ursane-and Oleanane-Tyoe Triterpene Oligoglycosides, Centellasaponins B, C, and D, from *Centella asiatica* Cultivated in Sira Lanka", Chem. Pharm. Bull, vol. 49, No. 10, pp. 1368-3171, 2000.
Sahu et al., "Spectroscopic Determination Of Structures Of Triterpenoid Trisaccharides From *Centella Asiatic*", Phytochemistry, vol. 28, No. 10, pp. 2852-2854, 1989.
Sampson et al., "In vitro keratinocyte antiproliferant effect of Centella asiatica extract and triterpenoid saponins", Phytomedicine, vol. 8, No. 3, pp. 230-235, 2001.
Pinhas, et al., "Structure de l'acida madecassique, nouveau triterpene de Centella asiatica de Madagascar", Extract de Bullenin de la Societe Chinique de France, No. 6, 1890-1895, 1967.
Pinhas et al., "Sur la constitute chimique de la patrie glucidique du madecassoside", Bulletin De La Societe Chimique de France, No. 6, pp. 1888-1889, 1967.
Srivastava et al., "Chemistry and pharmacology of *Centella asiatica: a review*", Journal of Medicinal and Aromatic Plant Sciences, vol. 19, pp. 1049-1056, 1997.
Database Bois 'online Biosciences Information Service, Philadelphia, PA, US, Coollins D J, et al., "Triterpene Acids From Some Papua New Guinea Terminalia Species" XP002251030, 1992.
Matsuda et al., "Medicinal Foodstuffs.XXVII[1]) Spanonin Constituents of Gotu Kola (2): Structures of New Ursane-and Oleanane-Tyoe Triterpene Oligoglycosides, Centellasaponins B, C, and D, from *Centella asiatica* Cultivated in Sira Lanka", Chem. Pharm. Bull, vol. 49, No. 10, pp. 1368-3171, 2000.
Maquart et al, "Triterpenes from Centella asiatica stimulate extracellular matrix accumulation in rat experimental wounds", Eur J Dermatol; 9; 289-96 (1999).
Inamdar et al, "Determination of biologically active constituents in Centella asiatica", Journal of Chromatography; A, 742; 127-130 (1996).
Bonte et al, "Asiaticoside and madecassoside activity on human fibroblast type I and III collagen secretion", Ann. Pharm. Fr., 53; 38-42 (1995).
Vogel, "Effect of Terpenoids Isolated from Centella Asiatica on Granuloma Tissue" Acta Therapeutica, 16; 285-298 (1990).
Sampson et al, "In Vitro Keratinocyte antiproliferant effect of Centella Asiatica extract and triterpenoid saponins", Phytomedicine 8(3); 230-235 (2001).
Inamdar et al, "Stability Study of the Active Constituents in the Centella asiatica Extract Formulations", Drug Development and Industrial Pharmacy, 22(3), 211-216 (1996).
Arch Dermatol Res; 265(6) 334-40 (1993).
J. Dermatol Sci; 17(3) 223-32 (1998).
Clin Dermatol; 21(5) 392-397 (2003).
J. Immunol; 175(4) 2721-9 (2005).
J Dermatol Sci; 7(I) 24-31 (1994).
Br J Dermatol; 136(4) 542-7 (1997).
Br J Pharmacol; 152, 353-365 (2007).
J Cell Physiol; 168(2) 442-52 (1996).
Int Arch Allergy Immunol; 116(1) 36-9 (1998). Arch Dermatol Res; 297 1-9 (2005).
Arch Dis Child; 70(2) 119-122 (1994).
Clin Exp Dermatol; 30(2) 160-64 (2005).
APMIS; 104(7-8) 509-514 (1996).
J. Rheumatol; 26(2) 251-258 (1999).
Clin Exp Rheumatol; 12(1) 55-58 (1994).
Pathol Biol Paris; 51(10) 569-73 (2003).
Mech Ageing Dev; 125(5) 359-66 (2004).
Photodermatol Photoimmunol Photomed; 17(4)178-83 (2001).
Mech Ageing Dev; 124(8-9) 903-910 (2003).
Photochem Photobiol; 78(1) 43-48 (2003).
J. Invest dermatol; 123(6)1012-1019 (2004).
Chin Med J 2006: 119(10): 827-831.
Punturee et al., Asian Pacific Journal of Cancer Prevention, 6; 396-400 (2005).

*Primary Examiner* — Elli Peselev

(74) *Attorney, Agent, or Firm* — Lerner, David, Littenberg, Krumholz & Mentlik, LLP

(57) ABSTRACT

The invention concerns an extract of *Centella asiatica* comprising more than 75 wt. % of a mixture of madecassoside, terminoloside and asiaticoside, relative to the extract total weight, an extract of *Centella asiatica* comprising more than 95 wt. % of a mixture of madecassoside and terminoloside relative to the extract total weight and their use for regulating inflammatory mechanisms.

27 Claims, No Drawings

METHOD FOR PREPARING A *CENTELLA ASIATICA* EXTRACT RICH IN MADECASSOSIDE AND IN TERMINOLOSIDE

CROSS-REFERENCE TO RELATED APPLICATIONS

This application is a continuation of application Ser. No. 10/537,936 filed Nov. 22, 2005, the disclosure of which is hereby incorporated by reference herein, which is a national phase entry under 35 U.S.C. §371 of International Application No. PCT/FR2003/003651 filed Dec. 10, 2003, published in French.

BACKGROUND OF THE INVENTION

The present invention relates to a method for preparing an extract comprising a mixture of madecassoside, of terminoloside and, where appropriate, of asiaticoside, an extract of *Centella asiatica* comprising more than 75 wt % of a mixture of madecassoside, of terminoloside and of asiaticoside, relative to the total weight of the extract, and an extract of *Centella asiatica* comprising more than 95 wt % of a mixture of madecassoside and of terminoloside relative to the total weight of the extract, and to their use for regulating inflammatory mechanisms.

*Centella asiatica*, also known as *Violette marronne* (Reunion island), as Gotu Kola or as Indian pennywort (India), or as *Centella repanda* (North America) and as Talapetraka (Madagascar), is a polymorphous herb that grows in the wild in humid and shady regions at an ideal altitude of 600 meters.

*Centella asiatica* belongs to the family of Umbelliferae (Apiaceae), particularly to the Hydrocotyle subfamily. *Centella* corresponds to the name of the genus of the plant, while *asiatica* corresponds to its species. *Centella asiatica* includes three varieties called *Typica, Abyssinica* and *Floridana*. *Centella asiatica* has been known and used in Madagascan, Indian, Chinese, American Indian or Indonesian medicine for more than 3000 years. It has varied and diverse uses according to countries. It is particularly advantageous for its healing, sedative, analgesic, antidepressant, antiviral and antimicrobial properties. It is generally used topically or orally. Paradoxically, the appearance of *Centella asiatica* in modern western medicine was late, since it made its entry into the Codex only in 1884, and the first dry extract was produced only in 1941.

The active agents of *Centella asiatica* are pentacyclic triterpenes, which are in the form of genins; these are asiatic acid (formula I) and madecassic acid (formula II), and of heterosides; these are asiaticoside (formula III) and madecassoside (formula IV).

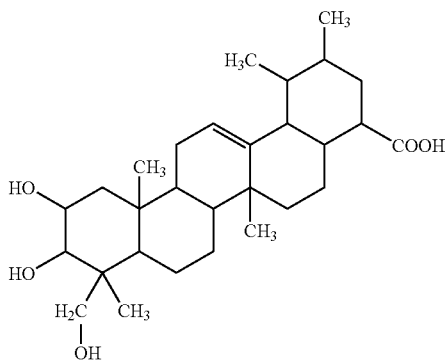

I

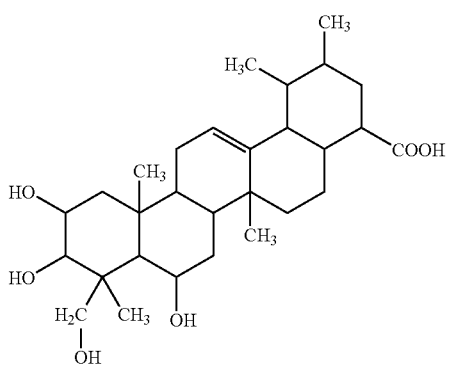

II

-continued

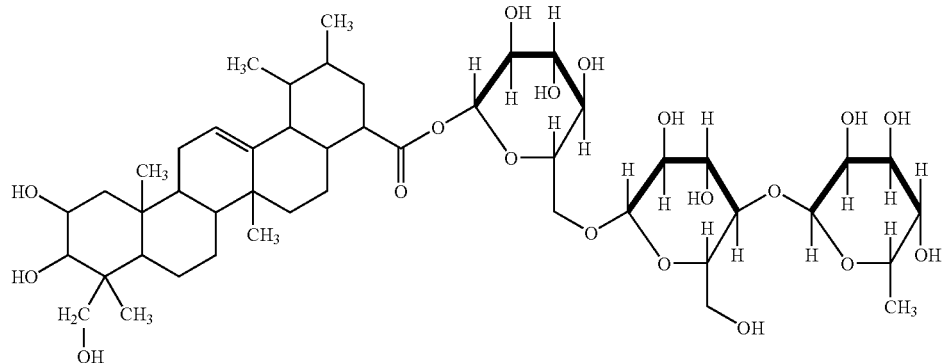

III

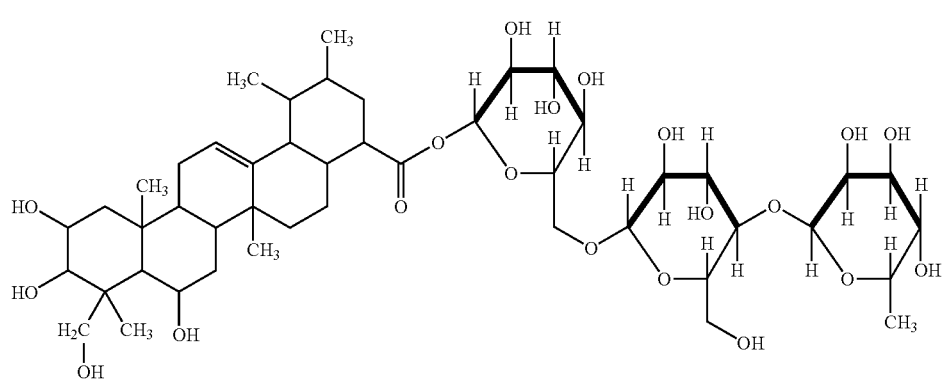

IV

Asiaticoside, madecassoside, asiatic acid and madecassic acid molecules contribute to the plant's natural defences. In order to be able to satisfactorily exploit the active agents of *Centella asiatica* industrially, it is therefore essential to collect the plant in the wild state, an environmental stress being necessary for this hardy plant to have a high triterpene content.

The *Centella asiatica* heterosides, madecassoside and asiaticoside, are sugar-containing complexes which constitute the storage forms of madecassic and of asiatic acid of the plant, synthesized essentially in the wet season. A bacterial, yeast or fungal attack on the plant activates the genin-releasing hydrolases. Triterpene molecules are particularly advantageous because of their regulatory and activating action on collagen synthesis. The genins and heterosides extracted from *Centella asiatica* promote in particular the synthesis of collagens 1 and 3. These active agents are used in the pharmaceutical field mainly for facilitating healing and in the treatment of venous insufficiency. They are used in the cosmetics field mainly as antiwrinkle and anticellulite agents. The active agents of *Centella asiatica* most commonly used in the prior art are asiatic acid and madecassic acid, and also asiaticoside. Since madecassoside is highly water-soluble, it is most commonly entrained in the washing water during conventional methods for extracting liposoluble active agents.

The methods of the prior art make it possible to obtain a mixture of asiaticoside and of madecassoside. This mixture comprises approximately 25 wt % of asiaticoside, 60 wt % of macecassoside and 15 wt % of by-products, mainly consisting of fatty acids and of osides, relative to the total weight of the mixture. Other methods of the prior art also make it possible to obtain madecassoside that is 81 wt % pure, relative to the total weight of the extract, said extract also comprising close isomers of madecassoside, fatty acids, mainly linoleic acid, linolenic acid, palmitic acid or oleic acid, and sugars such as osides.

Surprisingly, the applicant has developed a novel method of extraction which makes it possible to obtain a mixture of madecassoside, of asiaticoside and of a novel molecule that has been called terminoloside, said mixture being more than 75 wt % pure relative to the total weight of the mixture, and to obtain a mixture of madecassoside and of terminoloside, obtained more than 95 wt % pure relative to the total weight of the mixture. Similarly, the applicant has discovered an extract of *Centella asiatica* comprising a mixture of madecassoside, of terminoloside and, where appropriate, of asiaticoside.

Surprisingly, the applicant has also discovered that the mixture of madecassoside and of terminoloside extracted from the parts of *Centella asiatica* that are above ground can be used in a drug for regulating inflammatory mechanisms.

In addition, the mixture of madecassoside, of terminoloside and of asiaticoside extracted from the parts of *Centella asiatica* that are above ground can be used in a cosmetic composition for preventing and delaying premature aging of the skin.

SUMMARY OF THE INVENTION

In the context of the present invention, the term "terminoloside" will be intended to mean the chemical molecule of general name 1-[O-α-L-rhamnopyranosyl-(1-4)-O-β-glucopyranosol-(1-6)]-O-β-D-glucopyranose 2α,3β,6β,23-tetrahydroxyolea-12-en-28-oate of formula V below:

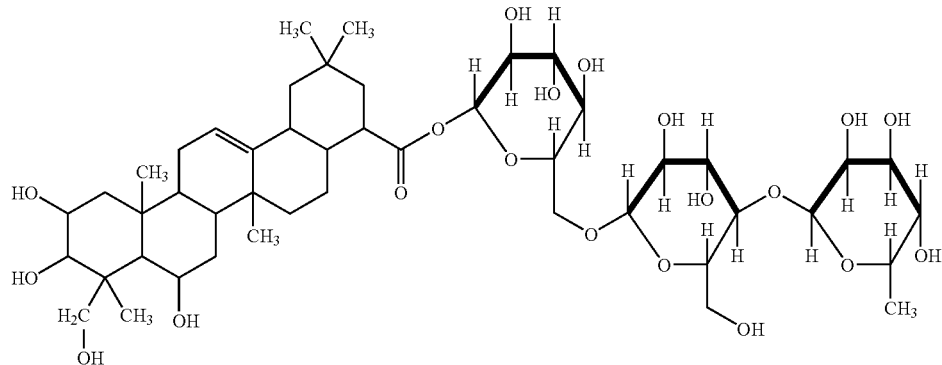

This molecule has the same sugar series as madecassoside, i.e. a glucose-glucose-rhamnose series. The structure of the terpene ring of terminoloside corresponds to that of the terpene ring of terminolic acid, of formula VI below:

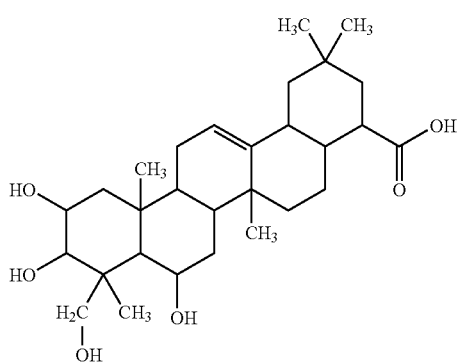

Terminoloside is thus a positional isomer of madecassoside. This molecule has never been isolated in the prior art. In addition, terminoloside has never been mentioned as being a possible extract of *Centella asiatica* and, consequently, no method for extracting terminoloside from *Centella asiatica* is known.

It could also be assumed that an undetected isomer of asiaticoside exists. Thus, in the context of the present invention, the term "asiaticoside" is intended to mean the chemical molecule of formula III, possibly as a mixture with one of its oleanic isomers, if it exists.

In the context of the present invention, the expression "binary mixture" will denote a mixture comprising mainly madecassoside and terminoloside, this mixture comprising virtually no asiaticoside, and the expression "ternary mixture" will denote a mixture comprising mainly madecassoside, terminoloside and asiaticoside.

A subject of the present invention is thus a method for preparing an extract comprising a mixture of madecassoside, of terminoloside and of asiaticoside, characterized in that it comprises the following steps:
 a) extraction of the parts of *Centella asiatica* that are above ground by means of an alcoholic solvent;
 b) passage of the alcoholic solution obtained in step a), over anionic resin;
 c) selective defatting by liquid/liquid extraction of the eluate obtained in step b);
 d) concentration of the defatted aqueous-alcoholic phase to an aqueous phase with successive filtrations;
 e) successive passage of the aqueous phase obtained in step d), over cationic resin and then over anionic resin;
 f) stabilization of the aqueous phase obtained in step e) by addition of alcohol and obtaining of a mixture comprising madecassoside, terminoloside and asiaticoside.

A subject of the present invention is a method for preparing an extract comprising a mixture of madecassoside and of terminoloside, characterized in that it comprises the following steps:
 a) extraction of the parts of *Centella asiatica* that are above ground by means of an alcoholic solvent;
 b) passage of the alcoholic solution obtained in step a), over anionic resin;
 c) selective defatting by liquid/liquid extraction of the eluate obtained in step b);
 d) concentration of the defatted aqueous-alcoholic phase to an aqueous phase with successive filtrations;
 e) successive passage of the aqueous phase obtained in step d), over cationic resin and then over anionic resin;
 f) stabilization of the aqueous phase obtained in step e) by addition of alcohol;
 g) selective chromatography of the prepurified aqueous-alcoholic phase obtained in step f); and
 h) recovery of the mixture of madecassoside and of terminoloside in its final form.

DETAILED DESCRIPTION OF THE INVENTION

The extraction of the active principles of the *Centella asiatica* plant is advantageously carried out using the parts of the plant that are above ground, with the main aim of not damaging its roots and thus of allowing the natural renewal of this hardy plant.

In an advantageous variant of the method according to the invention, the parts that are above ground are macerated in an alcoholic solvent before the extraction step. The alcoholic solvents that can be used according to the present invention are those conventionally used by those skilled in the art, such as ethanol and in particular 70% ethanol. The alcoholic solution thus obtained is then purified by means of a passage over an anionic resin (step b)). The anionic resin used in the method according to the invention is advantageously a strong anionic resin that has functional groups of the quaternary ammonium type. This passage of the alcoholic solution over an anionic resin makes it possible to trap the anionic by-products, in particular phenolic substances.

According to an advantageous variant of the method according to the invention, the alcoholic solution obtained subsequent to step a) is clarified before it is passed over the anionic resin. This advantageous clarification step consists in adding to said alcoholic solution a solution of strong base, such as a solution of sodium hydroxide, and activated charcoal. The addition of strong bases allows the precipitation, and thus the elimination by filtration, of the metals and of the other substances present that are capable of reacting with these strong bases. The addition of activated charcoal makes it possible, in addition, to decolor the alcoholic solution, by purifying it, and to fix fatty acids or oxidation products.

Subsequent to step b) consisting of passage over resin, advantageously preceded by a clarification step, the eluate obtained is purified with respect to these fatty fractions. For this, it is subjected to a liquid/liquid extraction. The extraction solvent used is an apolar solvent, advantageously an alkane such as heptane. Any of the liquid/liquid extraction methods known to those skilled in the art can be set up in the context of the present method according to the invention. In particular, said extraction may be a centrifugation. Since madecassoside is water-soluble, the aqueous-alcoholic phase is recovered.

The aqueous-alcoholic phase thus obtained is then concentrated to an aqueous phase and successively filtered, advantageously several times in a row, so as to allow precipitation of the compounds that are insoluble in the aqueous phase.

Subsequent to these first steps of the method according to the invention, an aqueous phase is obtained in which the two known heterosides of *Centella asiatica*, i.e. asiaticoside and madecassoside, and also the terminoloside are soluble. This aqueous phase is then purified by successive passage on a cationic resin and then on an anionic resin. This step consisting of successive passage on cationic resin and then on anionic resin is an essential step of the method according to the invention. Advantageously, the cationic resin used is a strong cationic resin that has functional groups of the sulfonate type. Advantageously, the anionic resin used is a strong anionic resin that has functional groups of the quaternary ammonium type. In the context of the method according to the invention, the order of the ion exchange resins is important in order to enhance the binding of residual acid fractions.

According to an advantageous variant of the invention, subsequent to the successive passages on cationic and then anionic resin of step e), and before step f), the aqueous phase obtained is also passed through activated charcoal. The activated charcoal thus makes it possible to take up the secondary phenolic compounds responsible for the coloration of the solution.

According to another advantageous variant of the invention, the aqueous phase obtained subsequent to step e), before step f), and optionally subsequent to a step consisting of passage over activated charcoal, undergoes one or more concentration step(s).

The aqueous phase obtained subsequent to step e), optionally after passage over activated charcoal and/or decoloration, is then stabilized by the addition of alcohol (step f)). A prepurified aqueous-alcoholic phase is then obtained in which the two known heterosides of *Centella asiatica* and the terminoloside are soluble. The mixture of madecassoside, terminoloside and asiaticoside is advantageously obtained with a purity of greater than 75 wt %, relative to the total weight of said mixture.

The prepurified aqueous-alcoholic phase obtained in step f) comprising the madecassoside, the terminoloside and the asiaticoside can then be purified by selective chromatography. The selective chromatography technique is well known to those skilled in the art. It makes it possible to separate the molecules according to their affinity with the stationary phase. This selective chromatography step makes it possible to separate the asiaticoside from the mixture consisting of the madecassoside and the terminoloside.

In the context of the present invention, the eluent used during the selective chromatography is a polar solvent. Advantageously, the solvent is a mixture of water and ethanol in water/ethanol proportions ranging from 50/50 to 90/10, and typically 75/25, volume/volume.

In the context of the present invention, the stationary phase used during the selective chromatography is an apolar stationary phase. Advantageously, the stationary phase consists of grafted apolar silicas. The apolar grafts advantageously have 2 to 18 carbon atoms, and even more advantageously 12 to 18 carbon atoms.

Subsequent to these steps of the method, i.e. to step h), a mixture of madecassoside and of terminoloside is obtained. The mixture advantageously has a madecassoside:terminoloside ratio of between 30 and 70 wt %, more advantageously of between 40 and 60 wt %. This mixture is advantageously obtained with a purity greater than 95 wt % relative to the total weight of said mixture. This binary mixture comprises virtually no more asiaticoside (only possibly in approximately trace amounts).

The subject of the present invention is also an extract of *Centella asiatica* that can be obtained by means of the method as described above and that comprises more than 95 wt % of a mixture of madecassoside and of terminoloside. The impurities present are in particular fatty acids. According to an advantageous variant of the invention, the mixture of madecassoside and of terminoloside has a ratio by mass of madecassoside with respect to the whole of between 30 wt % and 70 wt % of madecassoside, advantageously of between 40 wt % and 60 wt % of madecassoside. Advantageously, the extract according to the invention is an anti-inflammatory and immunomodulatory agent.

According to another advantageous variant of the invention, the method according to the invention can also comprise a parallel step consisting of standardization of the mixture of madecassoside, of terminoloside and of asiaticoside (ternary mixture), obtained subsequent to step f), by the addition of an appropriate amount of a very pure extract of *Centella asiatica* according to the invention, i.e. of a mixture of madecassoside and of terminoloside having a purity of greater than 95% (binary mixture), that can be obtained by means of the method according to the invention subsequent to step h), such that the final extract thus obtained has a purity of between 90 and 98 wt %, relative to the total weight of the final extract. The ternary mixture is thus standardized by the addition of the binary mixture so as to fix the final extract thus obtained within a range representing a purity of between 90 and 98 wt %, relative to the total weight of the final extract. For example, to obtain a final extract having a purity of 90%, 1 part of the binary mixture will be mixed with 1 part of the ternary mixture; to have a final purity of 98%, 9 parts of the binary mixture will be mixed with 1 part of the ternary mixture.

A subject of the present invention is also a standardized extract of *Centella asiatica* that can be obtained subsequent to the standardization step of the method according to the invention and that comprises at least 75 wt %, advantageously at least 85 wt %, of a mixture of madecassoside, of terminoloside and of asiaticoside (standardized tertiary mixture). The other impurities present are in particular fatty acids. In this standardized extract of *Centella asiatica*, the asiaticoside:(madecassoside+terminoloside) ratio by mass is advantageously between 5:95 and 25:75. If the percentage by mass of asiaticoside is too great, there is a risk of phase separation. Specifically, asiaticoside is organosoluble whereas madecassoside and terminoloside are water-soluble. The mixture consisting of madecassoside and of terminoloside is so water-soluble that it can solubilize up to approximately 25 wt % of asiaticoside. In this standardized extract of *Centella asiatica*, the madecassoside:terminoloside ratio by mass is advantageously between 30:70 and 70:30, even more advantageously between 40:60 and 60:40.

A subject of the present invention is also a drug comprising an extract of *Centella asiatica* comprising more than 95 wt % of a mixture of madecassoside and of terminoloside or a standardized extract of *Centella asiatica*, as described above, and a pharmaceutically acceptable support. For practical pharmacological reasons, a binary mixture rather than a ternary mixture is preferably used as a drug.

Madecassoside and terminoloside can hydrolyze, in particular upon contact with the flora of the skin, respectively to madecassic acid and to terminolic acid. However, these respective acids show no immunomodulatory activity.

When a foreign body, such as a bacterium or a virus, enters our body, the latter initiates a defence system, called immune system, to combat it. The immune system has to eliminate the foreign body without however destroying its own organism. In an autoimmune disease, the immune system no longer recognizes as its own certain "self" structures of the organism; it becomes deregulated and capable of attacking these "self" structures.

In the particular case of psoriasis, the antigens of the organism, circumvented by the immune defence, attack the individual's skin, which results in a drift toward inflammation. The hyperreaction of the regulatory system results in hyperproliferation of keratinocytes and therefore the formation of very thick and nonhomogeneous plaques of keratinocytes and of corneocytes. The drug according to the invention is intended to inhibit the pathological production of immune defences. Said drug is advantageously intended for regulating inflammatory mechanisms. More advantageously, said drug is intended for the treatment of autoimmune diseases, chronic inflammatory diseases, atopic inflammatory diseases or bowel diseases. Advantageously, said drug is intended for the treatment of psoriasis, vitiligo, pityriasis, scleroderma, bullous dermatoses, eczema, atopic dermatitis, allergy or rheumatoid arthritis.

In the dermatological field, the drug according to the invention is also intended for the prevention and treatment of drifting toward chronic inflammation associated with aging and its consequences. Said drug is advantageously intended for the prevention and treatment of diseases chosen from anaphylactic sensitizations, pigmentary anomalies of the skin, dermal hypervasculation and inflammatory fissuring. Said drug is also advantageously intended for regulating dermal tissue homeostasis, via a cellular protection and stimulation that results in enhancement of the extracellular matrix contributing to dermal-epidermal interaction.

A subject of the present invention is also a cosmetic composition comprising a standardized extract of *Centella asiatica* as described above and a cosmetically acceptable support. Said cosmetic composition is advantageously used for preventing any pathological drift toward autoimmunity that may result from natural aging of the skin. Said cosmetic composition is also advantageously used for delaying natural aging at the level of enhancement of cell functionality. Said cosmetic composition is even more advantageously used for preventing accelerated aging of skin subjected to outside attacks, in particular for protecting photo-induced aging of the skin.

The outside environment permanently attacks the skin, whether via ultraviolet radiation or via the radiation emitted by discharge lamps, or the various natural atmospheric antigens or atmospheric antigens existing due to human activity, urban pollution, etc., which initiates biological processes that accelerate natural aging. The anti-inflammatory system is thus permanently in action, which results in an acceleration of keratinocyte renewal in the skin, or even hyperproliferation, worsening the entropy of the tissue through overexpression of specific proteins and, in the end, loss of functionality. The consequence thereof is a renewal that depletes the natural reserves of keratinocyte cells, leading to premature aging of the skin. The cosmetic use of the composition according to the invention advantageously makes it possible to inhibit inflammatory disorders and thus to prevent aging of the skin.

The drug or the cosmetic composition is advantageously in a solid, pasty or liquid form. Advantageously according to the present invention, the drug or the cosmetic composition is formulated so as to be administered topically, orally, subcutaneously, by injection, rectally, and via the genital route. Advantageously according to the present invention, when the drug or the cosmetic composition is formulated so as to be administered topically, said drug or said composition is in the form of an aqueous solution, a white or colored cream, an ointment, a milk, a lotion, a gel, a salve, a serum, a paste, a foam, an aerosol, a shampoo or a stick. Advantageously according to the present invention, when the drug or cosmetic composition is formulated so as to be administered orally, said drug or said composition may be in the form of an aqueous solution, an emulsion, tablets, gelatin capsules, capsules, powders, granules, solutions or oral suspensions. Advantageously according to the present invention, when the drug or the cosmetic composition is formulated so as to be administered subcutaneously, said drug or said composition may be in the form of sterile injectable ampoules. Advantageously according to the present invention, when the drug or the cosmetic composition is formulated so as to be administered rectally, said drug or said composition may be in the form of suppositories. Advantageously according to the present invention, when the drug or the cosmetic composition is formulated so as to be administered via the genital route, said drug or said composition may be in the form of ovules.

The amount of the drug according to the invention to be administered depends on the seriousness of the treated condition and on how long the treated condition has been present. Naturally, the physician will also adjust the dosage according to the patient. The treatment of patients suffering from an autoimmune disease, with the extract of *Centella asiatica* containing more than 95 wt % of the mixture of madecassoside and of terminoloside with respect to the total weight of the mixture, consists in particular of the topical administration of said drug in a proportion of 1 to 3 wt %, relative to the volume of the excipient, of said extract in the transdermal carrier, per day once or twice. Particularly advantageously, the administration of said drug at doses as defined above is divided into 1 to 3 daily administrations.

The following examples illustrate the invention without however limiting the scope thereof.

Example 1

Composition of a Cream According to the Invention

TABLE 1

| Ingredients: INCI | w/w % |
|---|---|
| Madecassoside/terminoloside extract according to the invention (purity > 95%) | 1.0% |
| Beheneth-10 | 1.5% |
| Beheneth-25 | 1.5% |
| Dycaprylyl Carbonate | 5.0% |
| Hexyl Laurate | 5.0% |
| Isohexadecane | 5.0% |
| Cetearyl Isononaoate | 5.0% |
| Dimethicone | 1.0% |
| Behenyl Alcohol | 2.0% |
| Hydrogenated Vegetable Glycerides | 2.0% |
| Phenoxyethanol & parabens | 0.5% |
| Tocopheryl Acetate | 0.5% |
| Demineralized water | qs 100 |
| Glycerol | 3.0% |
| Butylene Glycol | 2.0% |
| Xanthan gum | 0.1% |
| Carbomer | 0.2% |

Example 2

Composition of a Cream According to the Invention

TABLE 2

| Ingredients: INCI | w/w % |
|---|---|
| Madecassoside/terminoloside extract according to the invention (purity > 95%) | 1% |
| Cetearyl Glucoside & Cetearyl Alcohol | 5.0% |
| Caprylic/Capric Triglyceride | 5.0% |
| Squalane | 5.0% |
| Cetearyl Isononanoate | 3.0% |
| Dimethicone crosspolymer | 2.0% |
| Stearyl Alcohol | 1.5% |
| Dycaprylyl Carbonate | 5.0% |
| Parabens | 0.1% |
| Demineralized water | qs 100 |
| Phenoxyethanol & Parabens | 0.5% |
| Glycerol | 2.0% |
| Carbomer | 0.3% |
| PEG 32 | 2.0% |
| Xanthan Gum | 0.2% |
| Aluminum starch octenyl succinate | 2.0% |

Example 3

Method for Extracting a Mixture of Madecassoside and of Terminoloside that is More than 95 Wt % Pure Relative to the Total Weight of the Extract a) Chemical Defecation and Purification of the Initial Alcoholic Liquor on a Column The parts of *Centella asiatica* that are above ground and that are used in this example comprise the leaves with approximately 2 to 3 cm of stalk. 250 kg of parts of *Centella asiatica* that are above ground are separated into three batches of equal amounts. The active principles of *Centella asiatica* are extracted from its parts above ground according to the principle of counter-current extraction. A batch of new parts of *Centella asiatica* that are above ground, i.e. parts that have not yet undergone any maceration or any filtration and are therefore very rich in active principles, is extracted once with a second extraction liquor, i.e. a depleted solvent almost saturated with active principles. The liquor thus obtained, that is called final liquor, is then directly sent to a chemical defecation tank. The batch is then subjected to a second extraction with a first maceration liquor, i.e. a liquor with a lower load than the liquor previously used and therefore capable of solubilizing more active principles. It is this liquor that is used as second extraction liquor. The batch is finally subjected to a third extraction with a fresh solvent which is thus capable of solubilizing the final percentages of active principles still present in the batch. It is this liquor that is used as first extraction liquor.

In the context of this example, the maceration and filtration solvent used is 70% ethanol. For 250 kg of parts of *Centella asiatica* that are above ground, 1600 l of 70% ethanol are used.

Depending on whether the preceding extraction step is carried out in a static tank or in a dynamic tank, the maceration time for the parts of *Centella asiatica* that are above ground, in 70% ethanol more or less saturated with active principles, ranges from one day to a few hours. In the specific case of dynamic tanks heated to a temperature of 60° C., the maceration time is two hours. 10 l of a 30% sodium hydroxide solution are then added to the final liquor, followed by 10 kg of activated charcoal, which makes it possible, by means of stirring, to decolor the solution. The solution is left to stir for 40 minutes and is then filtered. The filtrate is passed through a strong anionic resin that has functional groups of the quaternary ammonium type, at a flow rate of 300 l/h.

The aqueous-alcoholic eluate thus obtained is then neutralized with sodium hydroxide to an apparent pH of between 5.3 and 6.9, and then subjected to a liquid/liquid extraction, which is advantageously centrifuged with heptane.

The defatted phase thus obtained is concentrated by means of continuous evaporation under reduced pressure at a temperature not exceeding 70° C. This concentration makes it possible to eliminate the asiaticoside contained in the defatted phase. The product is concentrated until a volume of ethanol corresponding to approximately 90 vol % of the initial volume of the defatted phase is recovered and until the asiaticoside precipitates from the defatted phase. This phase is then filtered and the mother liquors are recovered. The madecassoside is so water-soluble that it solubilizes approximately 20 wt % of the asiaticoside having precipitated during the preceding concentration step.

b) Steps Consisting of Preparation of a Prepurified Aqueous-Alcoholic Phase

The concentrated aqueous phase recovered is purified by passage over cationic resin and then over anionic resin. The cationic resin is a strong cationic resin that has functional groups of the sulfonate type. The anionic resin is a strong anionic resin that has functional groups of the quaternary ammonium type. The eluate thus obtained is an aqueous-alcoholic phase which is then neutralized with hydrochloride acid to a pH between 6.75+/−0.25 and decolored by passage over activated charcoal.

The solution thus obtained is filtered and then concentrated, in a reactor under reduced pressure, until an aqueous phase is obtained, according to the same principle as the preceding concentration. It is then readjusted by adding ethanol in order to obtain a stabilized aqueous-alcoholic solution having a solids content of 200 g+/−20 per liter and an alcohol percentage of 35%+/−3.5% volume/volume. A prepurified phase rich in madecassoside and in terminoloside and still containing asiaticoside is thus obtained.

c) Purification Step

The prepurified aqueous-alcoholic phase thus obtained is then subjected to separation by selective chromatography. During this selective chromatography, the stationary phase used is a phase consisting of grafted apolar silicas, the apolar grafts having 18 carbon atoms and measuring 10 μm. The solvent used is a mixture of 65 vol % water and 35 vol % ethanol relative to the total volume of the mixture. The eluate thus obtained is concentrated, dried, and ground. These various steps make it possible to obtain a dry extract of *Centella asiatica*.

The dry extract contains 99.8 wt %, relative to the total weight of the extract, of a 51:49 mixture by mass of madecassoside and of terminoloside (binary mixture).

Example 4

Method for Extracting and Preparing a Standardized Mixture of Madecassoside, Terminoloside and Asiaticoside The extraction method is identical to that described in Example 3 as far as the step consisting of obtaining a prepurified phase rich in madecassoside and in terminoloside and still containing asiaticoside (before the purification step): ternary mixture.

This prepurified phase has a purity in terms of madecassoside, terminoloside and asiaticoside of 80 wt %. The impurities present are in particular fatty acids. If the amounts of madecassoside, of terminoloside and of asiaticoside are related back to 100%, the mixture comprises approximately 39 wt % of madecassoside, 39 wt % of terminoloside and 22 wt % of asiaticoside.

This extract is standardized by adding 100 wt % of the binary mixture obtained in Example 3 (i.e. as much ternary mixture as binary mixture).

A standardized extract of *Centella asiatica* that is 90 wt % pure is then obtained. This extract comprises, if the amounts of madecassoside, of terminoloside and of asiaticoside are related back to 100%, 45.7 wt % of madecassoside, 44.5 wt % of terminoloside and 9.8 wt % of asiaticoside.

Example 5

Isolation of the Two Madecassoside and Terminoloside Isomers 300 mg of a mixture of madecassoside and of terminoloside are chromatographed on a preparative column (of the brand Hypurity C18 (250×4.6)) having an 81:19 v/v water: acetonitrile mobile phase, at 30° C. The detection is carried out at a wavelength of 210 nm. 95 mg of terminoloside and 85 mg of madecassoside are thus obtained.

The chemical structure of madecassoside and of terminoloside is confirmed by spectrometric analysis ($^1$H NMR, $^{13}$C NMR and mass spectrometry).

Example 6

Evaluation of the Modulatory Effects of the Mixture of Madecassoside and of Terminoloside with Respect to Cell Growth in Hyperproliferative Human Keratinocytes In this example and in the following examples, the extract contains 99.8 wt % of the mixture of madecassoside and of terminoloside according to the invention relative to the total weight of the extract, said mixture containing 51 wt % of madecassoside and 49 wt % of terminoloside, relative to the total weight of the mixture.

Since the extract according to the invention mainly contains the mixture of madecassoside and of terminoloside, said extract will be denoted without distinction, in this example and in the following examples, by the expression "a mixture of madecassoside and of terminoloside" or by the expression "a mixture according to the invention".

The subject of this example is the evaluation of the modulatory effects of the mixture of madecassoside and of terminoloside with respect to cell growth in hyperproliferative human keratinocytes. The example was performed on human keratinocytes HaCaT stimulated with keratinocyte growth factor (hereinafter referred to as KGF) and/or human leukocyte elastase (hereinafter referred to as HLE).

a) Study of the Cytotoxicity of the Mixture of Madecassoside and of Terminoloside This cytotoxicity study consists in determining the maximum dose of product that does not result in cell toxicity. The cytotoxicity was studied on HaCaT human keratinocytes seeded into 96-well plates at a rate of $20 \times 10^3$, broad range, and $10 \times 10^3$, limited range, cells per well. The cell viability is evaluated by means of a colorimetric assay with Neutral Red. Neutral Red is a weakly cationic dye that penetrates cell membranes by means of a nonionic diffusion phenomenon and binds intracellularly to the phosphate and/or carboxylic groups of the lysosomal matrix. Modifications in the accumulation and retention of Neutral Red are observed when the cell membranes are damaged. The optical density of the solution obtained after incubation of the cells in the presence of Neutral Red is therefore proportional to the number of living cells.

A broad range of 9 concentrations, from 0.001 to 1 mg/ml, was initially tested. The various test solutions were prepared in DMEM medium, Dulbecco's Modified Essential Medium, supplemented with 10 vol % of FCS, fetal calf serum. After 24 hours of contact, the concentrations less than or equal to 1 mg/ml induce no significant modification of the cell response with respect to Neutral Red. A very small decrease in the uptake of Neutral Red, corresponding to 10% inhibition, is observed only at the highest concentration tested, of 1 mg/ml. Based on these results, a limited range, between 0.05 and 5 mg/ml, was established in order to specify the maximum noncytotoxic dose. The cell viability was evaluated by means of a Neutral Red calorimetric assay, after 72 hours of incubation. The results confirm the nontoxicity of the concentrations less than or equal to 1 mg/ml. From 1 mg/ml, a slight dose-dependent cytotoxic effect is observed. The highest concentration tested, 5 mg/ml, inhibits the cell response with respect to Neutral Red by 43%.

A second limited range of between 0.075 and 5 mg/ml was tested. The assay was carried out on HaCaT cells, after solubilization of the mixture of madecassoside and of terminoloside in dimethyl sulfoxide, hereinafter referred to as DMSO, at a concentration of 1%. The cell viability was evaluated by means of a Neutral Red calorimetric assay, after 72 hours of incubation. The results obtained were similar to those recorded in the absence of DMSO.

Table 3 below groups together all the results; the cell viability is expressed as percentage of the control assay.

TABLE 3

| | Concentration (mg/ml) | | | | | | | | |
|---|---|---|---|---|---|---|---|---|---|
| | 0.05 | 0.075 | 0.1 | 0.25 | 0.5 | 0.75 | 1 | 2.5 | 5 |
| Broad range (24 h) | 102% | n.t. | 105% | n.t. | 100% | n.t. | 90% | n.t. | n.t. |
| Limited range No. 1 (72 h) | 99% | 100% | 98% | 99% | 97% | 96% | 91% | 80% | 57% |
| Limited range No. 2 (72) | n.t. | 102% | 101% | 99% | 97% | 94% | 91% | 78% | 55% |

The abbreviation n.t. means not tested.

Given these results, it was decided to select the concentration of 300 µg/ml, as maximum dose, for testing the antiproliferative activity of the mixture of madecassoside and of terminoloside.

b) Effect on Cell Proliferation:

The principle of the assay is based on the evaluation of the growth of hyperproliferative human keratinocytes in the absence and in the presence of the mixture of madecassoside or of terminoloside. The method is based on measuring the cell densities in the cultures stimulated with KGF or with HLE. The cell densities are assessed by means of a calorimetric assay with Neutral Red. The absorbance of the solutions is read at 540 nm using a microplate reader.

4 concentrations of the mixture of madecassoside and of terminoloside were tested:

$C_1 = 10$ µg/ml $C_2 = 30$ µg/ml $C_3 = 100$ µg/ml $C_4 = 300$ µg/ml b.1) Stimulation with KGF:

6 test batches are prepared: a control batch (nonstimulated cells), a KGF control batch (cells stimulated with KGF at a concentration of 100 ng/ml) and 4 treated batches (cells stimulated with KGF and treated with the mixture of madecassoside and of terminoloside). The optical densities are measured at t=0 days, t=2 days and t=5 days. The means of the optical densities, O.D., are converted to cell densities, cells/well, using the regression line: O.D.=$0.00355 \times (10^3$ cells/well$)+0.0018$.

Table 4 below groups together the cell densities recorded after 2 and 5 days after activation of the cells with KGF.

TABLE 4

| Stimulation KGF | Treatment 2 days | | Treatment 5 days | |
|---|---|---|---|---|
| | Cells/well | Cell growth | Cells/well | Cell growth |
| Control without KGF | 56465 +/− 2486 | | 115802 +/− 988 | |
| Control with KGF | 85833 +/− 1742 | 100% | 157616 +/− 6359 | 100% |
| $C_1$ and KGF | 84388 +/− 2616 | 98% n.s. | 161354 +/− 5165 | 102% n.s. |
| $C_2$ and KGF | 85304 +/− 1312 | 99% n.s. | 161248 +/− 4232 | 102% n.s. |
| $C_3$ and KGF | 84317 +/− 1444 | 98% n.s. | 152081 +/− 2536 | 96% n.s. |
| $C_4$ and KGF | 83259 +/− 1960 | 97% n.s. | 150071 +/− 7087 | 95% n.s. |

The abbreviation n.s. means that the result is not statistically significant.

The results obtained show no significant modification of the growth of the HaCaT cells stimulated with KGF, after 2 or 5 days of culture in the presence of the mixture according to the invention.

b.2) Stimulation with HLE:

6 test batches are prepared: a control batch (nonstimulated cells), an HLE control batch (cells stimulated with HLE at a concentration of 3 nM, i.e. 90 ng/ml) and 4 treated batches (cells stimulated with HLE and treated with the mixture of madecassoside and of terminoloside). The optical densities are measured at t=0 days, t=2 days and t=5 days. The means of the optical densities, O.D., are converted to cell densities, cells/well, using the regression line: O.D.=$0.00458 \times (10^3$ cells/well$)+0.041$.

Table 5 below groups together the cell densities recorded after 2 and 5 days after activation of the cells with HLE.

TABLE 5

| Stimulation HLE | Treatment 2 days | | Treatment 5 days | |
|---|---|---|---|---|
| | Cells/well | Cell growth | Cells/well | Cell growth |
| Control without HLE | 66668 +/− 1380 | | 89180 +/− 2202 | |
| Control with HLE | 875973 +/− 1400 | 100% | 157616 +/− 6359 | 100% |
| $C_1$ and HLE | 76764 +/− 799 | 101% n.s. | 114584 +/− 2463 | 100% n.s. |
| $C_2$ and HLE | 75891 +/− 1190 | 100% n.s. | 115539 +/− 1261 | 101% n.s. |
| $C_3$ and HLE | 73408 +/− 1690 | 97% (p ≤ 0.05) | 112428 +/− 1548 | 98% (p ≤ 0.05) |
| $C_4$ and HLE | 72016 +/− 1597 | 95% (p ≤ 0.05) | 93355 +/− 1429 | 82% (p ≤ 0.05) |

The abbreviation n.s. means that the result is not statistically significant.

p ≤ 0.05 means that the results are statistically significant, with an error of 0.05%.

The results obtained show a slight decrease in the growth of the HaCaT cells stimulated with HLE, after 2 or 5 days of culture in the presence of the mixture according to the invention. This slight inhibitory effect only appears at the high concentrations. At 300 µg/ml, the mixture of madecassoside and of terminoloside reduces by 18%, relative to the control, the growth of the cells activated with HLE, after 5 days of treatment.

c) Conclusion:

In conclusion, KGF, at a concentration of 100 ng/ml, and HLE, at a concentration of 90 ng/ml, stimulate the growth of HaCaT cells.

The mixture of madecassoside and of terminoloside is not capable, within the range of concentrations tested, of modulating the growth of HaCaT cells stimulated with KGF. The mixture according to the invention is capable of modulating, in a dose-dependent manner, the growth of HaCaT cells stimulated with HLE. The mixture of madecassoside and of terminoloside at the dose of 300 µg/ml is capable of reducing by 18% the growth of HaCaT cells stimulated with HLE.

Example 7

Demonstration of the Anti-Inflammatory Activity of the Mixture of Madecassoside and of Terminoloside on Human Keratinocytes in Culture The subject of this example is the evaluation of the anti-inflammatory activity of the mixture according to the invention on the production and the release of pro-inflammatory epidermal cytokines, IL-1α and PGE-2, by human keratinocytes in culture, subjected to an irritative stress.

a) Study of the Cytotoxicity of the Mixture of Madecassoside and of Terminoloside This cytotoxicity study was carried out in the same manner as in Example 4 and the same results were obtained. In addition, added to the cytotoxicity study was an assay on human keratinocytes, strain $K_{02-1}H_4$, in order to confirm that the concentrations were nontoxic on the target cells.

A range of 8 concentrations, from 0.075 to 5 mg/ml was studied. The mixture of madecassoside and of terminoloside solubilized beforehand in DMSO was added to the culture medium at the selected concentrations; the final concentration of DMSO is 1%. The cell viability was determined by means of a Neutral Red assay.

The results confirm the nontoxicity of the concentrations less than or equal to 2.5 mg/ml, after 72 hours of incubation. The highest concentration tested, of 5 mg/ml, results in a 30% inhibition of the uptake of Neutral Red.

Table 6 below groups together the results. The cell viability is expressed as percentage of the control assay.

TABLE 6

| | Concentration (mg/ml) | | | | | | | |
|---|---|---|---|---|---|---|---|---|
| | 0.075 | 0.1 | 0.25 | 0.5 | 0.75 | 1 | 2.5 | 5 |
| Viability (72 h) | 98% | 96% | 102% | 96% | 93% | 98% | 95% | 70% |

Given these results, it was decided to select the concentration of 1 mg/ml as maximum dose, for testing the anti-inflammatory activity of the mixture of madecassoside and of terminoloside.

b) Anti-Inflammatory Activity:

The principle of the assay is based on evaluating the production of pro-inflammatory cytokines by human keratinocytes in response to an irritative stress. The method is based on measuring the intracellular amount of IL-1α and the amount of PGE-2 released into the extracellular medium by keratinocytes cultured in the absence and in the presence of the mixture of madecassoside and of terminoloside and stimulated with PMA, i.e. with phorbol-1,2-myristate-13-acetate.

The study was carried out on keratinocytes isolated from foreskin of young children, strain $K_{02-1}H_4$. 3 concentrations of the mixture of madecassoside and of terminoloside were tested:

$C_1$=0.1 mg/ml $C_3$=0.5 mg/ml $C_3$=1.0 mg/ml b.1) Release of PGE-2:

Table 7 below groups together the amounts of PGE-2, expressed as pg/µg of protein, obtained after activation of the cells, and also the basal amounts. The production of PGE-2 induced by PMA and the anti-inflammatory activity (subsequently referred to as AIA) were calculated for each concentration according to:

TABLE 7

| Mixture of madecassoside and of terminoloside | 0 mg/ml control cultures | 0.1 mg/ml | 0.5 mg/ml | 1 mg/ml |
|---|---|---|---|---|
| PGE-2 without PMA | 4.96 +/− 0.52 | 4.96 +/− 0.52 | 4.96 +/− 0.52 | 4.96 +/− 0.52 |
| PGE-2 with PMA | 39.34 +/− 2.64 | 18.73 +/− 0.67 | 10.69 +/− 0.50 | 6.60 +/− 0.44 |
| PGE-2 production | 34.38 +/− 2.64 | 13.77 +/− 0.67 | 5.73 +/− 0.50 | 1.64 +/− 0.44 |
| Anti-inflammatory activity (%) | | 60% | 83% | 95% |

Exposure of the keratinocytes to PMA results in a very substantial production and release of PGE-2 into the culture media of the control cultures. Specifically, the basal amount recorded in the nonstimulated cultures is multiplied 8-fold after stimulation with PMA. These results confirm that PGE-2 is a cytokine for which the expression, the production and the release can be induced using an inflammatory agent such as PMA.

The amounts of PGE-2 recorded after stimulation with PMA in the cultures treated with the mixture of madecassoside and terminoloside are very clearly lower than those observed in the control cultures. This inhibitory effect of the mixture according to the invention with respect to the PMA-induced release of PGE-2 is dose-dependent. The differences recorded in the batches $C_1$, $C_2$ and $C_3$ were found to be statistically significant ($p \leq 0.01$, Student's t test). The highest concentration of the mixture of madecassoside and of terminoloside that was tested, of 1 mg/ml, is capable of completely inhibiting the PMA-induced production of PGE-2.

b.2) Intracellular IL-1α Production:

Table 8 below groups together the intracellular amounts of IL-1α, expressed as pg/µg of protein, obtained after activation of the cells, and also the basal levels. The PMA-induced production of IL-1α and the anti-inflammatory activity (subsequently referred to as AIA) were calculated for each concentration according to:

$$IL\text{-}1\alpha \text{production} = IL\text{-}1\alpha_{with\ PMA} - IL\text{-}1\alpha_{without\ PMA}$$

and $$AIA = [(IL\text{-}1\alpha\text{production}_{control\ cells} - IL\text{-}1\alpha\text{production}_{treated\ cells})/IL\text{-}1\alpha\text{production}_{control\ cells}] \times 100$$

TABLE 8

| Mixture of madecassoside and of terminoloside | 0 mg/ml control cultures | 0.1 mg/ml | 0.5 mg/ml | 1 mg/ml |
| --- | --- | --- | --- | --- |
| IL-1α without PMA | 2.88 +/− 0.23 | 2.88 +/− 0.23 | 2.88 +/− 0.23 | 2.88 +/− 0.23 |
| IL-1α with PMA | 12.11 +/− 0.41 | 8.94 +/− 0.11 | 6.86 +/− 0.47 | 4.70 +/− 0.30 |
| IL-1α production | 9.23 +/− 0.41 | 6.06 +/− 0.11 | 3.98 +/− 0.47 | 1.82 +/− 0.30 |
| Anti-inflammatory activity (%) | | 34% | 57% | 80% |

Exposure of the keratinocytes to PMA results in a very substantial production and release of IL-1α into the culture media of the control cultures. Specifically, the basal amount recorded in the nonstimulated cultures in multiplied 4-fold after stimulation with PMA. These results confirm that IL-1α is a cytokine for which the expression, the production and the release can be induced using an inflammatory agent such as PMA.

The amounts of IL-1α recorded after stimulation with PMA in the cultures treated with the mixture of madecassoside and of terminoloside are clearly lower than those observed in the control cultures. This inhibitory effect of the mixture according to the invention with respect to the PMA-induced production and accumulation of IL-1α is dose-dependent. The differences recorded in the batches $C_1$, $C_2$ and $C_3$ were found to be statistically significant ($p \leq 0.01$, Student's t test). The highest concentration of the mixture of madecassoside and of terminoloside that was tested, of 1 mg/ml, is capable of reducing by 80% the PMA-induced production of IL-1α.

c) Conclusion:

The anti-inflammatory activity of the mixture of madecassoside and of terminoloside was evaluated on an in vitro model through its ability to modulate the production of two epidermal cytokines, PGE-2 and IL-1α, that play a key role in the steps of the inflammatory process. The study was carried out on cultures of normal human keratinocytes stimulated with an irritative agent, PMA. This example shows that PMA, at a nontoxic dose of 10 ng/ml, firstly, induces a very clear increase in the amount of intracellular IL-1α and, secondly, brings about the production and release of PGE-2 into the culture media.

The mixture of madecassoside and of terminoloside is capable of very clearly decreasing the PMA-reduced release of PGE-2. The mixture at a dose of 1 mg/ml is capable completely inhibiting the release of PGE-2. The mixture according to the invention is capable of modulating, in a dose-dependent manner, the PMA-induced production and intracellular accumulation of IL-1α.

Given the important roles of these two cytokines in the inflammatory process, the ability, shown by the mixture of madecassoside and of terminoloside, to modulate in a dose-dependent manner the expression and the release of PGE-2 and also the production of IL-1α by keratinocytes stimulated in vitro can be considered to be an anti-inflammatory activity.

Example 8

Evaluation of the Anti-Inflammatory Activity of the Mixture of Madecassoside and of Terminoloside On Human Keratinocytes in Culture The subject of this example is the evaluation of the anti-inflammatory activity of the mixture of madecassoside and of terminoloside on the production of TNF-α and of IL-8 induced by interferon-γ.

a) Cytotoxicity Study

This cytotoxicity study was carried out in the same manner as in Example 4 and the same results were obtained.

Given these results, it was decided to select the concentration of 1 mg/ml as maximum dose, for testing the anti-inflammatory activity of the mixture of madecassoside and of terminoloside.

b) Effect of Interferon-γ on the Production of Epidermal Cytokines

The study is carried out on normal human keratinocytes. The cells are first treated with 4 concentrations of interferon-gamma (IFN-γ), for 24 hours.

Next, the inflammation mediators are measured in the control cultures and cultures treated with IFN-γ, by assaying IL-8 and TNF-α in the culture supernatants and by assaying cell proteins. The method of measurement used is the Coomassie blue test; it is a standardized method. The results are given in Tables 9 and 10 below:

TABLE 9

| IL-8 (pg/µg proteins) | Control | Interferon-γ (U/ml) | | | |
| --- | --- | --- | --- | --- | --- |
| | 0 | 100 | 500 | 1000 | 2000 |
| Mean | 0.077 | 0.980 | 1.301 | 1.991 | 2.917 |
| Standard deviation | 0.060 | 0.119 | 0.102 | 0.113 | 0.138 |

TABLE 10

| TNF-α (pg/µg proteins) | Control | Interferon-γ (U/ml) | | | |
| --- | --- | --- | --- | --- | --- |
| | 0 | 100 | 500 | 1000 | 2000 |
| Mean | 3.260 | 3.198 | 8.605 | 10.773 | 14.545 |
| Standard deviation | 0.519 | 0.744 | 1.195 | 1.673 | 1.256 |

The results obtained show that interferon-γ, in the range of concentrations tested, from 100 to 2000 U/ml, induces in a dose-dependent manner a clear stimulation of the production of TNF-α and of IL-8. The letter U is the abbreviation for unit; 1 U corresponds to one unit of interferon-γ.

In the case of the epidermal cytokine TNF-α, the basal amount recorded in the nonstimulated cultures is multiplied, respectively, 3.3-fold and 4.5-fold after stimulation with interferon at 1000 and 2000 U/ml. In the case of the epidermal cytokine IL-8, the basal amount recorded in the nonstimulated cultures is multiplied, respectively, 26-fold and 38-fold after stimulation with interferon at 1000 and 2000 U/ml.

These results confirm that interferon is capable of stimulating the expression, the production and the release of these two epidermal cytokines. In view of these results, it was decided to select the concentration of 1000 U/ml for stimulating the keratinocytes.

c) Anti-Inflammatory Activity of the Mixture of Madecassoside and of Terminoloside The study is carried out on normal human keratinocytes. The cells are first treated, for 48 h, with the product being studied, before induction of the irritative stress. Next, an irritative stress is induced by adding a solution of interferon-γ, IFN-γ. The cells thus activated are incubated for 24 h in the presence of the product being studied. Finally, the amounts of IL-8 and of TNF-α in the culture supernatants are assayed and the cell proteins are also assayed.

c.1) Results Regarding the Cytokine IL-8:

The tables below group together the amounts of IL-8, expressed as pg/μg of proteins, obtained after activation of the cells, and also the basal amount. The anti-inflammatory activity (AIA) was calculated for each concentration according to the formula:

$$AIA = [(IL\text{-}8_{(control\ cells+IFN)} - IL\text{-}8_{(treated\ cells+IFN)}) / IL\text{-}8_{(control\ cells+IFN)}] \times 100$$

The results of the samples of keratinocytes treated with the mixture of madecassoside and of terminoloside are given in Table 11 below:

IL-8 is very clearly lower than that observed in the cultures of the control batch. The highest concentration of the mixture of madecassoside and of terminoloside is capable of inhibiting by 63% the IFN-γ-induced release of IL-8. The differences recorded in the batches C1, C2, C3 and C4 were found to be statistically significant ($p \leq 0.01$, Student's t test) compared with the control batch.

c.2) Results Regarding the Cytokine TNF-α:

The tables below group together the amounts of TNF-α (pg/mg proteins) obtained after activation of the cells, and also the basal amount. The anti-inflammatory activity (AIA) was calculated for each concentration according to the formula:

$$AIA = [(TNF\text{-}\alpha_{(control\ cells+IFN)} - TNF\text{-}\alpha_{(treated\ cells+IFN)}) / TNF\text{-}\alpha_{(control\ cells+IFN)}] \times 100$$

The results of the samples of the keratinocytes treated with the mixture of madecassoside and of terminoloside are given in Table 12 below:

TABLE 12

|  | Control without IFN | Control with IFN 0 mg/ml | IFN and mixture of madecassoside + terminoloside | | | |
|---|---|---|---|---|---|---|
|  |  |  | 0.1 mg/ml | 0.25 mg/ml | 0.5 mg/ml | 1 mg/ml |
| TNF-α (pg/μg prot.) | 2.39 +/− 0.16 | 5.26 +/− 0.31 | 4.95 +/− 0.22 | 4.97 +/− 0.24 | 4.67 +/− 0.15 | 3.92 +/− 0.10 |
| Anti-inflammatory activity |  |  | 6% | 6% | 11% | 26% |

The results obtained show a substantial production and release of TNF-α into the control culture media after stimulation with interferon-γ, at a concentration of 100 U/ml. The basal amount recorded in the nonstimulated cultures is multiplied 2.2-fold after stimulation with IFN-γ, at a concentration of 1000 U/ml. The results obtained also show a slight decrease, that is dose-dependent, in the amount of TNF-α in the treated cultures stimulated with IFN-γ. The highest concentration of the mixture of madecassoside and of terminoloside is capable of inhibiting by 26% the IFN-γ-induced release of TNF-α.

d) Conclusion

The anti-inflammatory activity of the mixture of madecassoside and of terminoloside was evaluated on an in vitro model through its ability to modulate the production of two epidermal cytokines, IL-8 and TNF-α, that play a key role in

TABLE 11

|  | Control without IFN | Control with IFN | | IFN and mixture of madecassoside + terminoloside | | |
|---|---|---|---|---|---|---|
|  |  | 0 mg/ml | 0.1 mg/ml | 0.25 mg/ml | 0.5 mg/ml | 1 mg/ml |
| IL-8 (pg/μg prot.) | 0.06 +/− 0.01 | 1.03 +/− 0.04 | 0.72 +/− 0.09 | 0.53 +/− 0.06 | 0.39 +/− 0.03 | 0.39 +/− 0.02 |
| Anti-inflammatory activity |  |  | 31% | 49% | 62% | 63% |

The results obtained show a very substantial production and release of IL-8 into the control culture media after stimulation with interferon-γ, at a concentration of 100 U/ml. The basal amount recorded in the nonstimulated cultures is multiplied 18-fold after stimulation with IFN-γ. Furthermore, these results also show a very substantial decrease, that is dose-dependent, in the amount of IL-8 in the treated cultures stimulated with IFN-γ. The interferon-induced production of the steps of the inflammatory process. The study was carried out on cultures of normal human keratinocytes stimulated with an irritative agent, IFN-γ.

This example shows that IFN-γ, at a nontoxic dose of 1000 U/ml, firstly, induces a very clear increase in the amount of IL-8 and, secondly, brings about the production and the release of TNF-α into the culture media. The mixture according to the invention is capable of modulating, in a dose-dependent manner, the IFN-γ-induced production and intracellular accumulation of IL-8. The mixture at the dose of 1 mg/ml is capable of inhibiting by 63% the release of IL-8.

The mixture of madecassoside and of terminoloside is capable of decreasing the IFN-γ-induced release of TNF-α. The mixture at the dose of 1 mg/ml is capable of inhibiting by 26% the release of TNF-α.

If the results obtained in a closed system, i.e. the assays carried out in vitro, were to be extrapolated to hypotheses for a mechanism of chemical activity that are effective in vivo, the following observations could be objectified: TNF-α is one of the activators of IL8 production, not only in keratinocytes, but also and especially in macrophages and B lymphocytes.

The fact that the mixture, firstly, only partially decreases the expression of TNF-α is, beyond the moderation of the expression of inflammatory signals, the manifestation of a control of the activity of an immune system that is not depressed since TNF-α performs a major role in the cellular control and monitoring of the skin, in particular in apoptotic phase. Secondly, this mixture decreases the expression of IL8, resulting in an attenuation of the chemotaxis of neutrophil and basophil polymorphonuclear cells and the consequences regarding a decrease in proteolytic "pressure", resulting in moderation of the propagation of the inflammatory signal and, in addition, a decrease in vascular permeability. Another consequence is, in return, the reduced activation of T lymphocytes of the skin by IL8.

Example 9

Effect of the Mixture of Madecassoside and of Terminoloside with Respect to the Production of SKALP by Human Keratinocytes The subject of this example is the evaluation of the antipsoriatic activity of the mixture of madecassoside and of terminoloside on the expression of cytokeratin 10, particularly of elafin, hereinafter abbreviated to CK10 or SKALP, by keratinocytes in a state of differentiation.

a) Cytoxicity Study

This cytotoxicity study was carried out in the same manner as in Example 4 and the same results were obtained. Given these results, it was decided to select the concentration of 1 mg/ml as maximum dose, for testing the anti-psoriatic activity of the mixture of madecassoside and of terminoloside.

b) Expression of SKALP and Differentiation of Keratinocytes

The study is carried out on normal human keratinocytes. The cells are placed in culture in three different media:

"proliferation" medium: KGM medium with gf, growth factor, medium supplemented with growth factors, "normal differentiation" medium: KGM medium without gf, medium depleted of growth factors, "psoriasis-type differentiation" medium: KGM medium with FCS, medium supplemented with fetal calf serum, hereinafter referred to as FCS (5%).

Next, the amount of SKALP in the incubation media for the cells cultured for 72 h in these various media is measured. The measurement assay is the ELISA assay described in Skin pharmacology and applied skin physiology, 2002; 15:152-261.

The results are as follows:
1. KGM medium with gf SKALP=1.17+/−0.18 ng/µg 100 proteins
2. KGM medium without gf SKALP=1.34+/−0.20 ng/µg 115 proteins
3. KGM medium with FCS SKALP=2.76+/−0.08 ng/µg 236 proteins The results obtained show that the expression of SKALP varies according to the state of differentiation of the cells. The production of SKALP is very clearly increased when the cells are cultured in medium containing FCS. The amount of SKALP in "psoriasis-type" differentiation medium is multiplied 2.4-fold compared with the amount of SKALP recorded in proliferation medium.

c) "Antipsoriatic" Effect of the Products Studied

The assay conditions are as follows: cells are placed in culture in "normal" differentiation medium, i.e. in KGM medium without gf, and in "psoriasis-type" differentiation medium, i.e. in KGM medium with FCS, in the absence, which corresponds to the control batch, and in the presence of the mixture according to the invention, for 72 h. The amount of SKALP in the culture supernatants is then assayed. The cell proteins are also assayed. Tables 13 and 14 below group together the amounts of SKALP, expressed as ng/µg proteins, obtained after culturing the cells in KGM medium without gf and in KGM medium with FCS.

α) Culturing in "Normal" Differentiation Medium: KGM Medium without gf

TABLE 13

| | KGM with gf | KGM without gf 0 mg/ml | KGM without gf + mixture according to the invention | | | |
|---|---|---|---|---|---|---|
| | | | 0.1 mg/ml | 0.25 mg/ml | 0.5 mg/ml | 1 mg/ml |
| SKALP (ng/µg prot.) | 1.17 +/− 0.18 | 1.34 +/− 0.20 | 1.01 +/− 0.24 | 1.15 +/− 0.16 | 1.05 +/− 0.18 | 0.53 +/− 0.14 |
| SKALP PRODUCTION | | 100% | 75% | 86% | 78% | 40% |

The results obtained show a decrease in the amount of SKALP in the cultures treated with the mixture according to the invention. Only the difference recorded in batch C4 was found to be statistically significant (p≦0.01, Student's t test) compared with the "KGM without gf" control. The highest concentration of the mixture of madecassoside and of terminoloside is capable of inhibiting by 60% the secretion of SKALP in "normal" differentiation medium.

β) Culturing in "Psoriasis-Type" Differentiation Medium: KGM Medium with FCS

TABLE 14

|  | KGM with gf | KGM with FCS 0 mg/ml | KGM with FCS + mixture according to the invention | | | |
|---|---|---|---|---|---|---|
|  |  |  | 0.1 mg/ml | 0.25 mg/ml | 0.5 mg/ml | 1 mg/ml |
| SKALP (ng/μg prot.) | 1.13 +/− 0.19 | 2.76 +/− 0.08 | 2.22 +/− 0.24 | 2.34 +/− 0.12 | 2.06 +/− 0.15 | 1.64 +/− 0.10 |
| SKALP PRODUCTION |  | 100% | 80% | 85% | 75% | 60% |

The results obtained show a dose-dependent decrease in the amount of SKALP in the cultures treated with the mixture according to the invention. The differences recorded in batches C1, C2, C3 and C4 were found to be statistically significant ($p \leq 0.01$, Student's t test) compared with the "KGM with FCS" control. The highest concentration of the mixture of madecassoside and of terminoloside is capable of inhibiting by 40% the secretion of SKALP in "psoriasis-type" differentiation medium.

d) Conclusion

The antipsoriatic activity of the mixture of madecassoside and of terminoloside was evaluated on an in vitro model through its ability to modulate the secretion of SKALP, which is thought to play a key role in diseases of the psoriasis type. The study was carried out on cultures of normal human keratinocytes in various media.

This example shows that the expression of SKALP varies according to the state of differentiation of the cells and increases very clearly in a "psoriasis-type" medium, i.e. containing FCS.

The mixture according to the invention is capable of inhibiting, in a dose-dependent manner, the secretion of SKALP in "normal" differentiation medium and in "psoriasis-type" differentiation medium. The mixture at the dose of 1 mg/ml is capable of inhibiting by 60% the secretion of SKALP in "normal" differentiation medium and of inhibiting by 40% the secretion of SKALP in "psoriasis-type" differentiation medium. Given the important role of the secretion of SKALP in psoriasis, the ability shown by the mixture of madecassoside and of terminoloside to modulate, in a dose-dependent manner, the secretion of SKALP by keratinocytes in various differentiation media in vitro can be considered to be an antipsoriatic activity. This result demonstrates the protective effect of the mixture according to the invention with respect to epidermal cells in the proteolytic context that characterizes a psoriasis-type model, according to a method of cellular desensitization in the context of the inflammatory hyperplasic reaction.

Example 10

Effects of the Mixture of Madecassoside and of Terminoloside on the Activation of NFκB in Fibroblast Cultures Nuclear factor-KB is a transcription factor that governs the expression of the genes encoding cytokines, chemokines, growth factors, cell adhesion molecules, and certain short-lived proteins. NFκB is activated by several agents, including cytokines, free radicals, inhaled particles, ultraviolet irradiation, and bacteria or viruses.

Inflammatory agents such as TNF-α induce the transcription of target proinflammatory genes via the activation, inter alia, of the NFκB transcription factor. Under nonstimulated conditions, the transcription factor NFκB is bound, in the cytoplasm, to an inhibitory protein IkB. The binding of TNF-α to its receptor results in the phosphorylation of this complex and in the dissociation of NFκB from the inhibitor. Activated NFκB then migrates into the nucleus and binds to a promoter sequence, called NFκB consensus sequence, specific for genes trans-activated by NFκB. This sequence brings about the transcription of the target genes. The activation of NFκB can therefore be measured by bringing stimulated or nonstimulated nuclear extracts into contact with NFκB consensus oligonucleotide sequences immobilized on supports, and quantifying bound NFκB using an immunoenzymatic method, such as ELISA with anti-NFκB antibodies.

This study makes it possible to evaluate the effects of the mixture according to the invention on the activation of NFκB, using a very sensitive specific method based on measuring the binding of the transcription factor NFκB to the consensus oligonucleotide sequence immobilized on a plastic support. Bound NFκB is secondarily recognized by a specific anti-NFκB antibody.

This assay was carried out on isolated nuclei of normal human fibroblasts.

The culture medium is DMEM, which comprises:
2 mM L-glutamine
50 IU/ml penicillin, 50 μg/ml streptomycin
10% (v/v) fetal calf serum for the preculture and then a switch to serum-free medium

TABLE 15

| Products assayed | Stock solution | Dilution | Final concentration tested |
|---|---|---|---|
| Mixture according to the invention | 10% in culture medium | Culture medium | 0.01% |

TABLE 16

| References | Stock solution | Dilution | Final concentration tested |
|---|---|---|---|
| Dexamethasone (Sigma D1756) | $10^{-2}$ M in DMSO | Culture medium | 0.1 μM |
| Sulfasalazine (Sigma S0883, MW 398.4) | 1 M in DMSO | Culture medium | 5 mM | a) Study of the Cytotoxicity of the Mixture of Madecassoside and of Terminoloside This cytotoxicity study was carried out in the same manner as in Example 4 and the same results were obtained. Given these results, it was decided to select the concentration of 0.01% as maximum dose, for testing the antipsoriatic activity of the mixture of madecassoside and of terminoloside.

b) Treatments, Extractions and Assays

The fibroblasts were precultured in 175 cm$^2$ flasks in DMEM medium containing 10 vol % of FCS until confluency, and the culture medium was then replaced with serum-free DMEM medium. The cells were then cultured in the presence of the products to be assayed or of references, for 1 hour. The proinflammatory agent transforming growth factor alpha (TNF-α, at 25 ng/ml final concentration; Sigma T0157) was then added to the culture medium and the cells were again incubated for 1 hour at 37° C. and 5% $CO_2$. After incubation, the cells were harvested on ice and the cell nuclei of the various samples were isolated using the Sigma NUC-101 kit according to the protocol recommended by the supplier. The amount of proteins of each nuclear extract was determined using the Biorad 500-0116 assay kit. The amount of activated NFκB bound to the specific oligonucleotide was measured on the same amount of nuclear extract of each sample, i.e. 50 μl, diluted 50/50, after visualization using a specific anti-NFκB antibody. This assay was carried out using the Mercury transfactor NFκB assay kit, BD Biosciences K2058-1, according to the protocol recommended by the supplier.

c) NFκB Assay

The results are given in Table 17 below:

TABLE 17

| Treatment | NFκB (AU) | mean | % control | P |
|---|---|---|---|---|
| Nontreated control | 10.71<br>8.39<br>8.90<br>10.19 | 9.55 | 100 | — |
| Control without TNF-α | 0.00<br>0.62<br>0.62<br>−0.21 | 0.26 | 3 | p < 0.01 |
| 5 mM sulfasalazine | 4.93<br>4.01<br>2.88<br>4.93 | 4.19 | 44 | p < 0.01 |
| 0.1 μM dexamethasone | 10.94<br>7.3<br>9.90<br>9.67 | 9.46 | 99 | p < 0.05 |
| 0.01% mixture according to the invention | 10.16<br>6.79<br>9.63<br>9.63 | 9.05 | 95 | p < 0.05 |

The basal amount of NFκB in the fibroblast nuclei is very low. The treatment with TNF-α at 25 ng/ml greatly activated the transcription factor NFκB, by a factor of approximately 37 compared with the TNF-α-free control. Controls using an excess of oligonucleotide made it possible to show that virtually the entire response observed was specific for the binding of NFκB. 5 mM sulfasalazine, the reference inhibitor for NFκB translocation, clearly reduced the activation of the transcription factor NFκB induced by TNF-α; 44% of the control with TNF-α, p<0.01.

0.1 μM dexamethasone did not inhibit the nuclear translocation of NFκB induced by TNF-α. In fact, dexamethasone represses the transactivation of NFκB-induced genes, but does not inhibit the activation of NFκB or its translocation to the nucleus. There is thus an inhibitory effect on the transcription but no effect on the translocation of NFκB; the action of dexamethasone takes place at the nuclear level, via the glucocorticoid receptor, it is therefore subsequent to the action of sulfasalazine.

The product according to the invention tested at 0.01% did not significantly modify the activation of NFκB induced by TNF-α, 95% of the control. This result does not exclude an anti-inflammatory activity via another mechanism.

d) Conclusion

The noninterference of madecassoside or of its isomer in the activation of NFκB results in the transcription of ligands, such as inflammatory cytokines and chemokines, which make the cell operational in the case of a pathogenic antigenic attack, being permitted.

Madecassocide and its isomer have no interaction with or against the activation of NFκB produced by fibroblasts. The moderation of inflammatory ligands in autoimmune deregulations, IL1, IL8, TNF-α, PGE2 at the membrane, indicates that madecassoside and its isomer would act rather at the translational level (better tolerance in the event of drift toward inflammation), and at the level of systems for expression and/or for synthesis of proteins, peptides or other ligands (less intracellular expression of ILs).

Example 11

In Vitro Evaluation of the Modulatory Effects of Asiaticoside and of a Mixture of Madecassoside and of Terminoloside (50/50 w/w) on the Production of Extracellular Matrix Metalloproteinases Via Human Fibroblasts Cultured in a Dermatitis Equivalent Model The object of this example is to evaluate the modulatory effects of asiaticoside and of a mixture of madecassoside and of terminoloside (50/50 w/w) on the protection of metalloproteinases (MMPs) and of their specific inhibitors (TIMPs) by human skin fibroblasts cultured in a dermous equivalent (collagen lattice). An in vitro experimental approach based on measuring the amounts of MMP-1 and of TIMP-1 released into the culture media by human fibroblasts cultured in the absence and in the presence of the products, and stimulated with TNF-α, is proposed. The study was carried out on human fibroblast cultures established from skin biopsies according to the explant method. The fibroblasts are cultured, according to the techniques used in the laboratory, in DMEM medium (sold under the name Invitrogen™ by the company Life Technologies) supplemented with fetal calf serum (10% FCS) and with antibiotics, at 37% in a humid air-$CO_2$ (95%-5%) atmosphere.

a) Cytotoxicity

This cytotoxicity study was carried out in the same manner as in Example 6.

Asiaticoside:

A stock solution of the product was prepared beforehand in DMSO and then diluted in culture medium in order to obtain the various test solutions (final concentration of DMSO: 1%). A broad range of 8 concentrations [from 5 to 1000 μg/ml] was initially studied in order to close in the maximum NonCytotoxic Dose (NCD). After contact for 24 h, no significant cytotoxic effect was recorded in the range of concentrations tested. Based on these results, a limited range of between 10 and 1000 μg/ml was established in order to specify the maximum NonCytotoxic Dose (NCD) after contact for 48 h. The results (Table 18) confirm the nontoxicity of the concentrations below 1 mg/ml after incubation for 48 h. The cell viability is decreased by only 12% when the cells are incubated in the presence of the active agent at 1 mg/ml.

TABLE 18

| | ASIATICOSIDE (pg/ml) | | | | | | | | |
|---|---|---|---|---|---|---|---|---|---|
| | 10 | 25 | 50 | 75 | 100 | 250 | 500 | 750 | 1000 |
| Viability (24 h) | 98% | 101% | 101% | n.t. | 101% | 101% | 97% | n.t. | 93% |
| Viability (48 h) | 108% | 107% | 106% | 104% | 102% | 99% | 93% | 90% | 88% |

Madecassoside-terminoloside mixture:

A stock solution of the product was prepared beforehand in DMSO and then diluted in culture medium in order to obtain the various test solutions (final concentration of the DMSO: 1%). A broad range of 8 concentrations (between 0.005 and 100 mg/ml) was studied on human fibroblasts in order to close in the maximum NonCytotoxic Dose (NCD). After contact for 24 h, the concentrations equal to 1 mg/ml induced no significant modification of the uptake of Neutral Red. Beyond this, a dose-dependent cytotoxic effect was recorded. Based on these results, a limited range of between 0.1 and 10 mg/ml was established in order to specify the maximum NonCytotoxic Dose (NCD).

The results (Table 19) confirm the nontoxicity of the concentrations equal to 1 mg/ml, after incubation for 48 h.

TABLE 19

| | Mixture of madecassoside and terminoloside (mg/ml) | | | | | | | | | |
|---|---|---|---|---|---|---|---|---|---|---|
| | 0.05 | 0.1 | 0.25 | 0.5 | 0.75 | 1 | 2.5 | 5 | 7.5 | 10 |
| Viability (24 h) | 98% | 98% | n.t. | 96% | n.t. | 94% | n.t. | 68% | n.t. | 60% |
| Viability (48 h) | n.t. | 101% | 96% | 97% | 99% | 99% | 99% | 86% | 71% | 47% |

Based on the cytotoxicity results, the "1 mg/ml" concentration was selected as Maximum NonCytotoxic Dose (NCD), for testing the asiaticoside and madecassoside-terminoloside mixture active agents with respect to the production of MMPs.

b) Production of Metalloproteinases

Human dermal fibroblasts cultured as a monolayer are detached from their support by trypsinization and suspended in complete medium. After counting, the cell suspension is diluted in culture medium and added, in defined proportions, to a mixture of concentrated culture medium (1.76×DMEM), fetal calf serum (FCS) and type I collagen (acetic acid extract from rat tail tendons). The mixture is then poured, under cold conditions, into 24-well plates in a proportion of 1 ml/well. The dermous equivalents are then placed at 37° C. and incubated for 72 h, in an air-$CO_2$ (95%/5%) atmosphere. The gels gradually contract under the action of the fibroblasts.

72 hours after seeding, the culture medium is removed and replaced with new medium containing the various products being studied ("preventative" treatment). The gels are returned to the incubator at 37° C. and incubated, for 24 hours, in an air-$CO_2$ (95%/5%) atmosphere.

After incubation, the cultures are emptied. The plates are rinsed and then exposed to a solution of TNF-α (10 ng/ml) in the absence (control cultures) or in the presence (treated cultures) of the various concentrations of each product being studied. After the addition of TNF-α, the cultures are returned to the incubator at 37° C. for 24 h. At the end of incubation, the media are removed, centrifuged and aliquoted for assaying of MMP-1 and of TIMP-1.

The study was carried out on human fibroblasts cultured in a three-dimensional gel of collagen (dermous equivalent).

Operating Conditions:
1. Treatment of cells for 24 h, before induction of MMP-1 with TNF-α.
2. Induction of MMP-1 by the addition of TNF-α (10 ng/ml). Incubation for 24 h.
3. Measurement of cell viability and of the amounts of MMP-1 in the control and treated culture supernatants.

Asiaticoside:

The asiaticoside was tested at 3 concentrations:
$C_1$=0.2 mg/ml $C_2$=0.5 mg/ml $C_3$=1.0 mg/ml Cell Viability (Neutral Red Assay)

The treatment of the cells with 10 ng/ml TNF-α results in no modification of the cell viability. No decrease in Neutral Red uptake is observed after exposure to TNF-α. Similarly, the viability of the cultures treated with asiaticoside is not modified after treatment with TNF-α.

Production of MMP-1

Table 20 below groups together the amounts of MMP-1 (ng/ml) obtained in the culture supernatants after activation of the cells (+TNF), and also the basal amounts (−TNF).

TABLE 20

| | Production of MMP-1 (ng MMP-1/ml) | | | |
|---|---|---|---|---|
| Collagen | (−) TNF-α | | (+) TNF-α | |
| gels treated with | mean | standard deviation | mean | standard deviation |
| Control | 2.24 | 0.54 | 12.11 | 1.03 |
| Asiaticoside (0.2 mg/ml) | not measured | | 9.96 | 0.47 |
| Asiaticoside (0.5 mg/ml) | not measured | | 6.18 | 0.15 |
| Asiaticoside (1.0 mg/ml) | not measured | | 3.40 | 0.21 |

In the control cells, the results obtained show that the TNF-α induces a clear stimulation of MMP-1 production. The basal amount recorded in the nonstimulated cells is multiplied 503-fold after stimulation with TNF-α.

In the treated cells, the amounts of MMP-1 recorded after stimulation with TNF-α in the cultures treated with asiaticoside are lower than that observed in the (+)TNF-α control.

The effect of asiaticoside with respect to the TNF-α-induced production of MMP-1 is dose-dependent. The differences recorded in the batches $C_1$ ($p \leq 0.05$), $C_2$ ($p \leq 0.01$) and $C_3$ ($p \leq 0.01$) were found to be statistically significant (Student's t test) relative to the (+)TNF-α control.

$C_1$: 18% decrease in the amount of MMP-1
$C_2$: 49% decrease in the amount of MMP-1
$C_3$: 72% decrease in the amount of MMP-1

Madecassoside-Terminoloside Mixture

The madecassoside-terminoloside mixture was tested at 3 concentrations:

$C_1$=0.2 mg/ml $C_2$=0.5 mg/ml $C_3$=1.0 mg/ml

Cell Viability (Neutral Red Assay)

The viability of the cultures treated with the madecassoside-terminoloside mixture is not modified after treatment with TNF-α.

Production of MMP-1

The results show a dose-dependent decrease in the amounts of MMP-1 in the supernatants of cultures treated with madecassoside-terminoloside mixture and stimulated with TNF-α. Only the differences recorded in the treated batches $C_2$ and $C_3$ are statistically significant (p≦0.01, Student's t test):

$C_1$: 3% decrease in the amount of MMP-1
$C_2$: 39% decrease in the amount of MMP-1
$C_3$: 61% decrease in the amount of MMP-1.

Table 21 below groups together the amounts of MMP-1 (ng/ml) obtained in the culture supernatants after activation of the cells (+TNF) and also the basal amounts (−TNF).

TABLE 21

| | Production of MMP-1 (ng MMP-1/ml) | | | |
|---|---|---|---|---|
| | (−) TNF-α | | (+) TNF-α | |
| Collagen gels treated with | mean | standard deviation | mean | standard deviation |
| Control | 2.24 | 0.54 | 12.11 | 1.03 |
| Madecassoside-terminoloside mixture (0.2 mg/ml) | not measured | | 11.78 | 0.83 |
| Madecassoside-terminoloside mixture (0.5 mg/ml) | not measured | | 7.37 | 0.76 |
| Madecassoside-terminoloside mixture (1.0 mg/ml) | not measured | | 4.76 | 0.52 | c) Production of TIMP-1

The amount of TIMP-1, an inhibitor specific for MMP-1, was also measured in the supernatants of the cultures treated with asiaticoside or the madecassoside-terminoloside mixture. Each active agent was tested at 3 concentrations:

C1=0.2 mg/ml C2=0.5 mg/ml and C3=1.0 mg/ml

Table 22 below groups together the amounts of TIMP-1 (ng/ml) obtained in the culture supernatants after activation of the cells (+TNF), and also the basal amounts (−TNF).

TABLE 22

| | Production of TIMP-1 (ng TIMP-1/ml) | | | |
|---|---|---|---|---|
| | (−) TNF-α | | (+) TNF-α | |
| Collagen gels treated with | mean | standard deviation | mean | standard deviation |
| Control | 51.20 | 1.22 | 48.90 | 2.16 |
| Asiaticoside (0.2 mg/ml) | not measured | | 51.01 | 1.51 |
| Asiaticoside (0.5 mg/ml) | not measured | | 50.36 | 1.67 |
| Asiaticoside (1.0 mg/ml) | not measured | | 48.82 | 2.22 |
| Madecassoside-terminoloside mixture (0.2 mg/ml) | not measured | | 48.63 | 1.18 |
| Madecassoside-terminoloside mixture (0.5 mg/ml) | not measured | | 46.98 | 2.02 |
| Madecassoside-terminoloside mixture (1.0 mg/ml) | not measured | | 48.76 | 0.92 |

The results obtained show that:

the production of TIMP-1 by fibroblasts cultured in a collagen gel is not modified by TNF-α;

the active agents consisting of asiaticoside and of the madecassoside-terminoloside mixture exert, within the range of concentrations tested, no effect with respect to the production of TIMP-1.

d) Conclusion:

The modulatory effects of the active agents consisting of asiaticoside and of the madecassoside-terminoloside mixture with respect to the production of metalloproteinases (MMPs) and of their specific inhibitors (TIMPs) was assessed, in vitro, on a model of human dermis. The study was carried out on normal human fibroblasts cultured in a three-dimensional collagen matrix. The effects of the active agents were evaluated by measuring the amounts of MMP-1 and TIMP-1 in the culture supernatants after activation of the cells with TNF-α.

Under the experimental conditions selected, the results of this study showed that:

TNF-α, at a noncytotoxic dose (10 ng/ml), induces a considerable increase in the production of MMP-1. On the other hand, the production of TIMP-1 is not modified after treatment of the cells with TNF-α;

the active agents consisting of asiaticoside and of the madecassoside-terminoloside mixture are capable of reducing, in a dose-dependent manner, the TNF-α-induced production of MMP-1. At the highest concentration tested (1 mg/ml), these two active agents are capable of reducing, respectively by 72% and 61%, the amount of MMP-1 induced by TNF-α;

the asiaticoside and the madecassoside-terminoloside mixture have, within the range of concentrations tested, no effect with respect to production of TIMP-1.

The study, carried out on human fibroblasts, makes it possible to observe, under the inflammatory stimulus of TNF-α, a considerable increase (530%) in release of MMP1 (collagenase) into the culture medium. The madecassoside-terminoloside mixture, like the asiaticoside, significantly decreases, in a dose-dependent manner, the concentration of MMP-1 (madecassoside-terminoloside mixture=−39% at 500 micrograms/kg and asiaticoside=−49%). The release of MMP1 inhibitors, TIMPs and in particular TIMP1, is not modified. This result is to be compared with the studies car ried out on the SKALPs (Example 9), since, in the presence of the madecassoside-terminoloside mixture, a high concentration of leukoproteases does not increase the secretion of inhibitors, but greatly decreases that of pro-inflammatory ligands by keratinocytes.

This also implies that the madecassoside-terminoloside mixture and the asiaticoside are active agents on the two dermal compartments, namely the epidermis and the dermis.

Example 12

Anti-Inflammatory Activity of Terminoloside, of Madecassoside and of the Mixture of Heterosides (Madecassoside, Terminoloside and Asiaticoside

In this example, the mixture of heterosides consists of 40 wt % of terminoloside, 40 wt % of madecassoside and 20 wt % of asiaticoside, relative to the total weight of the mixture.

In order to evaluate the anti-inflammatory activity of terminoloside, of madecassoside and of the mixture of heterosides, we studied the modulatory effects of these three active agents with respect to the production and release of proinflammatory epidermal cytokines (IL-1α, IL-8, PGE-2) by human keratinocytes in culture, subjected to an irritative stress induced either with interferon-gamma (IFN-γ) or with PMA. Human keratinocytes were isolated from human skin. The cells were cultured in serum-free KGM medium (Keratinocyte Growth Medium, sold by the company Clonetics®), according to the usual techniques set up in the laboratory, at 37° C. in a humid air-$CO_2$ (95%-5%) atmosphere. The cells were seeded into 25 $cm^2$ flasks and passaged regularly before reaching confluency. The principle of the assay is based on evaluating the production of proinflammatory cytokines by human keratinocytes, in response to an irritative stress. The method is based on measuring the intracellular amount of IL-1α and of the amounts of IL-8 and of PGE-2 released into the extracellular medium by keratinocytes cultured in the absence and in the presence of the products being studied, and stimulated even with interferon-gamma (IFN-γ) or with PMA (phorbol-12-myristate-13-acetate).

a) Cytotoxicity

This cytotoxicity study was carried out in the same manner as in Example 6 on HaCaT human keratinocytes and on normal human keratinocytes.

Terminoloside:

Cytotoxicity on Hacat Human Keratinocytes

Table 23 below groups together all the results (cell viability as % of control)

TABLE 23

| | Concentration (mg/ml) | | | | | | | | | |
|---|---|---|---|---|---|---|---|---|---|---|
| | 0.05 | 0.1 | 0.25 | 0.5 | 0.75 | 1 | 2.5 | 5 | 7.5 | 10 |
| Viability (24 h) | 105% | 104% | 105% | 105% | n.t. | 104% | 100% | 81% | n.t. | 73% |
| Viability (72 h) | n.t. | 100% | 101% | 101% | 103% | 102% | 103% | 93% | 86% | 69% | n.t.: not tested

After contact for 24 h, the concentrations ≦2.5 mg/ml induce no significant modification of the cellular response with respect to RN. Beyond 2.5 mg/ml, a slight dose-dependent cytotoxic effect is recorded.

Cytotoxicity on Human Keratinocytes

Added to the cytotoxicity study was an assay on human keratinocytes (strain $K_{02-1}H_4$) in order to confirm the nontoxicity of the concentrations on the "target" cells. Table 24 below groups together all the results (cell viability as % of control).

TABLE 24

| | Concentration (mg/ml) | | | | | | |
|---|---|---|---|---|---|---|---|
| | 0.25 | 0.5 | 0.75 | 1.0 | 2.5 | 5 | 10 |
| Viability (72 h) | 101% | 103% | 103% | 102% | 99% | 96% | 69% |

The results confirm the nontoxicity of the concentrations less than or equal to 2.5 mg/ml after incubation for 72 h.

madecassoside:

Cytotoxicity on Hacat Human Keratinocytes

Table 25 below groups together all the results:

TABLE 25

| | Concentration (mg/ml) | | | | | | | | | |
|---|---|---|---|---|---|---|---|---|---|---|
| | 0.05 | 0.1 | 0.25 | 0.5 | 0.75 | 1 | 2.5 | 5 | 7.5 | 10 |
| Viability (24 h) | 105% | 102% | 103% | 99% | n.t. | 100% | 85% | 75% | n.t. | 63% |
| Viability (72 h) | n.t. | 101% | 102% | 102% | 101% | 101% | 92% | 76% | 71% | 56% |

After contact for 24 h, the concentrations less than 1.0 mg/ml induce no significant modification of the cellular response with respect to RN. Beyond 1.0 mg/ml, a slight dose-dependent cytotoxic effect is recorded.

Cytotoxicity on Human Keratinocytes

Added to the cytotoxicity study was an assay on human keratinocytes (strain $K_{02-1}H_4$) in order to confirm the nontoxicity of the concentrations on the "target" cells.

Table 26 below groups together all the results (cell viability as % of control).

TABLE 26

| | Concentration (mg/ml) | | | | | | |
|---|---|---|---|---|---|---|---|
| | 0.25 | 0.5 | 0.75 | 1.0 | 2.5 | 5 | 10 |
| Viability (72 h) | 102% | 101% | 102% | 101% | 97% | 88% | 72% |

The results confirm the nontoxicity of the concentrations less than 2.5 mg/ml. Beyond this, a slight dose-dependent cytotoxic effect is recorded.

Heterosides:

Cytotoxicity on HaCat Human Keratinocytes

Table 27 groups together all the results (cell viability as % of control).

TABLE 27

| | Concentration (mg/ml) | | | | | | | | |
|---|---|---|---|---|---|---|---|---|---|
| | 0.1 | 0.25 | 0.5 | 0.75 | 1 | 2.5 | 5 | 7.5 | 10 |
| Viability (24 h) | 102% | 103% | 99% | 100% | 85% | 85% | 75% | n.t. | 63% |
| Viability (72 h) | 100% | 101% | 97% | 95% | 97% | 90% | 80% | 74% | 38% |

After contact for 24 h, the concentrations less than 1.0 mg/ml induce no significant modification of the cellular response with respect to RN. Beyond 1.0 mg/ml, a slight dose-dependent cytotoxic effect is recorded.

Cytotoxicity on Human Keratinocytes

Added to the cytotoxicity study was an assay on human keratinocytes (strain $K_{02-1}H_4$) in order to confirm the nontoxicity of the concentrations on the "target" cells. Table 28 groups together all the results (cell viability as % of control).

TABLE 28

| | Concentration (mg/ml) | | | | | | |
|---|---|---|---|---|---|---|---|
| | 0.1 | 0.25 | 0.5 | 0.75 | 1.0 | 2.5 | 5 | 10 |
| Viability (72 h) | 97% | 97% | 99% | 93% | 88% | 64% | 34% | 12% |

The results confirm the nontoxicity of the concentrations less than 0.75 mg/ml. Beyond this, a slight dose-dependent cytotoxic effect is recorded. Based on these results, the concentration equal to 1 mg/ml was selected as maximum dose for testing the anti-inflammatory activity of the three active agents.

b) Effect of Interferon-γ

The effects of interferon-gamma (IFN-γ) on the production and release of epidermal cytokines was studied on normal human keratinocytes (strain $K_{02-1}H_4$). 4 concentrations of IFN-g were tested:

$C_1$=100 U/ml $C_2$=500 U/ml $C_3$=1000 U/ml $C_4$=2000 U/ml

Production of Intracellular IL-1α

The results are given in Table 29 below:

TABLE 29

| IL-1α (pg/μg proteins) | Control | Interferon-γ (U/ml) | | | |
|---|---|---|---|---|---|
| | 0 | 100 | 500 | 1000 | 2000 |
| Mean | 3.25 | 6.80 | 8.29 | 11.21 | 12.48 |
| Standard deviation | 0.05 | 0.12 | 0.12 | 0.73 | 0.80 |

The results obtained show that interferon-γ, within the range of concentrations tested, induces, in a dose-dependent manner, a clear stimulation of intracellular IL-1α production. The basal amount recorded in the nonstimulated cells (3.25+/−0.05 pg/μg prot.) is multiplied, respectively, 2.6-fold and 3.8-fold after stimulation with IFN-γ at 1000 and 2000 pg/ml.

Release of IL-8

The effects of IFN-γ on the production and release of IL-8 were studied under the same experimental conditions. The results are given in Table 30 below:

TABLE 30

| IL-8 (pg/μg proteins) | Control | Interferon-γ (U/ml) | | | |
|---|---|---|---|---|---|
| | 0 | 100 | 500 | 1000 | 2000 |
| Mean | 0.093 | 0.252 | 0.350 | 0.516 | 0.671 |
| Standard deviation | 0.013 | 0.042 | 0.009 | 0.004 | 0.048 |

The results obtained in the cultures not stimulated with IFN-γ (—IFN-γ) confirm the absence or the presence of very small amounts of IL-8 in the incubation media for keratinocytes in the basal state. On the other hand, a clear stimulation of the production and release of IL-8 is recorded after stimulation with IFN-γ. This dose-dependent increase in the amount of intracellular IL-8 in the cultures (+IFNγ) confirms the role of this proinflammatory cytokine on the production and release of IL-8.

Release of PGE-2

The effects of IFN-γ on the production and release of PGE-2 was studied under the same experimental conditions as previously described (Table 31).

TABLE 31

| Extracellular PGE-2 (pg/μg proteins) | Control | Interferon-γ (U/ml) | | | |
|---|---|---|---|---|---|
| | 0 | 100 | 500 | 1000 | 2000 |
| Mean | 10.49 | 3.60 | 3.45 | 3.48 | 3.80 |
| Standard deviation | 3.16 | 0.61 | 0.32 | 0.74 | 0.13 |

The results show that IFNγ is not capable of stimulating, within the range of concentrations tested, the production and release of PGE-2.

c) Anti-Inflammatory Activity:

The study was carried out on keratinocytes isolated from foreskin of young children (strain $K_{02-1}H_6$).

Each active agent, terminoloside, madecassoside and heterosides, was tested at 4 concentrations:

$C_1$=0.01 mg/ml $C_2$=0.25 mg/ml $C_3$=0.50 mg/ml $C_4$=1.00 mg/ml

Assay Conditions:

1. Treatment of the cells for 48 h with the product being studied before induction of the irritative stress; 2. induction of the irritative stress: IFN-γ (1000 U/ml); 3. incubation of the "activated" cells, for 24 h, in the presence of the product being studied; 4. assay: IL-8 (extracellular) and IL-1α (intracellular). Cellular protein assay.

Release of IL-8

Tables 32 to 34 below group together the amounts of IL-8 obtained after activation of the cells (+IFN-γ), and also the basal amounts (—IFN-γ). The IFN-γ-induced production of IL-8 and the anti-inflammatory activity (AIA) were calculated, for each concentration of active agent, according to:

$$AIA = [(IL\text{-}8_{(control\ cells+IPN)} - IL\text{-}8_{(treated\ cells-IPN)} / IL\text{-}8_{control\ cells+IFN})] \times 100$$

of IL-8.

TABLE 32

Terminoloside

| | Control (−IFN-γ) | Control (+IFN-γ) | IFN-γ + TERMINOLOSIDE | | | |
|---|---|---|---|---|---|---|
| | — | 0 mg/ml | 0.1 mg/ml | 0.25 mg/ml | 0.5 mg/ml | 1 mg/ml |
| IL-8 (pg/μg prot) | 0.099 +/− 0.005 | 0.843 +/− 0.026 | 0.862 +/− 0.076 | 0.762 +/− 0.052 | 0.708 +/− 0.030 | 0.492 +/− 0.014 |
| Anti-inflammatory activity (%) | | | 0% | 9% | 15% | 42% |

A very substantial release of IL-8 is observed in the control cultures after stimulation with IFN-γ. The very small basal amount recorded in the nonstimulated cultures indicates that IL-8 is not present at the basal state, but that its expression and its release can be induced with IFN-γ. The basal amount is multiplied 8.5-fold after stimulation with IFN-γ. The amounts of IL-8 recorded after stimulation with IFN-γ in the cultures treated with the active agent terminoloside are lower than that of the (+)IFN-γ control.

The effect of the active agent terminoloside with respect to the IFN-γ-induced release of IL-8 is dose-dependent. The differences recorded in the batches $C_2$ ($p \leq 0.05$), $C_3$ ($p \leq 0.01$) and $C_4$ ($p \leq 0.01$) were found to be statistically significant (Student's t test) relative to the (+)IFN-γ control. The highest concentration tested (1 mg/ml) is capable of reducing by 42% the IFN-γ-induced production of IL-8.

TABLE 33

Madecassoside:

| | Control (−IFN-γ) | Control (+IFN-γ) | IFN-γ + MADECASSOSIDE | | | |
|---|---|---|---|---|---|---|
| | — | 0 mg/ml | 0.1 mg/ml | 0.25 mg/ml | 0.5 mg/ml | 1 mg/ml |
| IL-8 (pg/μg prot) | 0.099 +/− 0.005 | 0.843 +/− 0.026 | 0.656 +/− 0.043 | 0.643 +/− 0.047 | 0.614 +/− 0.039 | 0.368 +/− 0.019 |
| Anti-inflammatory activity (%) | | | 21% | 24% | 27% | 56% |

The results show a dose-dependent decrease in IL-8 in the batches treated with madecassoside and stimulated with IFN-γ. The differences in the batches $C_1$, $C_2$, $C_3$ and $C_4$ are statistically significant ($p \leq 0.01$, Student's t test). The 1 mg/ml concentration is capable of reducing by 56% the production

TABLE 34

| | | Heterosides: | | | |
|---|---|---|---|---|---|
| | Control (−IFN-γ) | Control (+IFN-γ) | IFN-γ + HETEROSIDES | | |
| | — | 0 mg/ml | 0.1 mg/ml | 0.25 mg/ml | 0.5 mg/ml | 1 mg/ml |
| IL-8 (pg/µg prot) | 0.099 +/− 0.005 | 0.843 +/− 0.026 | 0.83 +/− 0.04 | 0.63 +/− 0.1 | 0.47 +/− 0.06 | 0.36 +/− 0.01 |
| Anti-inflammatory activity (%) | | | 1% | 25% | 44% | 57% |

The results show a dose-dependent decrease in IL-8 in the batches treated with the mixture of heterosides (madecassoside, terminoloside and asiaticoside) and stimulated with IFN-γ. The differences in the batches $C_1$, $C_2$, $C_3$ and $C_4$ are statistically significant ($p \leq 0.01$, Student's t test). The 1 mg/ml concentration is capable of reducing by 57% the production of IL-8.

Production of Intracellular IL-1α

Tables 34 to 36 below group together the intracellular amounts of IL-1α after activation of the cells (+IFN-γ), and the basal amount (—IFN-γ). The IFN-γ-induced production of IL-1α and the anti-inflammatory activity (AIA) were calculated for each concentration according to:

TABLE 35

| | Terminoloside | | | | | |
|---|---|---|---|---|---|---|
| | Control (−IFN-γ) | Control (+IFN-γ) | IFN-γ + TERMINOLOSIDE | | | |
| | — | 0 mg/ml | 0.1 mg/ml | 0.25 mg/ml | 0.5 mg/ml | 1 mg/ml |
| IL-1α (pg/µg prot) | 2.71 +/− 0.09 | 10.04 +/− 0.44 | 8.78 +/− 0.77 | 8.08 +/− 0.43 | 7.31 +/− 0.38 | 5.02 +/− 0.13 |
| IL-1α production | | 7.33 | 6.07 | 5.37 | 4.60 | 2.31 |
| Anti-inflammatory activity (%) | | | 17% | 27% | 37% | 68% |

In the (+IFN-γ) control batch, the basal amount of IL-1α is multiplied 3.7-fold after treatment with IFN-γ, confirming that IL-1α is a cytokine for which the intracellular production can be induced with IFN-γ. A clear decrease in the amount of IL-1α is recorded in the cultures treated with the active agent terminoloside. The inhibitory effect is dose-dependent. The differences in $C_1$ ($p \leq 0.05$), $C_2$ ($p \leq 0.01$), $C_3$ ($p \leq 0.01$) and $C_4$ ($p \leq 0.01$) are statistically significant (Student's t test) relative to the (+IFN-γ) control.

The active agent at 1 mg/ml is capable of reducing by 68% the IFN-γ-induced production of IL-1α.

TABLE 36

| | Madecassoside | | | | | |
|---|---|---|---|---|---|---|
| | Control (−IFN-γ) | Control (+IFN-γ) | IFN-γ + MADECASSOSIDE | | | |
| | — | 0 mg/ml | 0.1 mg/ml | 0.25 mg/ml | 0.5 mg/ml | 1 mg/ml |
| IL-1α (pg/µg prot) | 2.71 +/− 0.09 | 10.04 +/− 0.44 | 8.23 +/− 0.57 | 8.23 +/− 0.64 | 8.07 +/− 0.69 | 6.05 +/− 0.37 |
| IL-1α production | | 7.33 | 5.52 | 5.52 | 5.36 | 3.34 |
| Anti-inflammatory activity (%) | | | 25% | 25% | 27% | 54% |

The results show a 54% decrease ($p \leq 0.01$) in the amount of IL-1α in the cultures treated with the active agent madecassoside at 1 mg/ml. On the other hand, the $C_1$, $C_2$ and $C_3$ concentrations appear to be equivalent: a 25% decrease ($p \leq 0.01$) in the amount of IL-1α is observed.

TABLE 37

Heterosides

|  | Control (−IFN-γ) | Control (+IFN-γ) | IFN-γ + HETEROSIDES | | | |
|---|---|---|---|---|---|---|
|  | — | 0 mg/ml | 0.1 mg/ml | 0.25 mg/ml | 0.5 mg/ml | 1 mg/ml |
| IL-1α (pg/µg prot) | 2.71 +/− 0.09 | 10.04 +/− 0.44 | 8.78 +/− 0.13 | 9.03 +/− 0.83 | 7.52 +/− 0.38 | 5.56 +/− 0.39 |
| IL-1α production |  | 7.33 | 6.07 | 6.32 | 4.81 | 2.85 |
| Anti-inflammatory activity (%) |  |  | 17% | 14% | 34% | 61% |

The results show a 61% decrease ($p \leq 0.01$) in the amount of IL-1α in the cultures treated with the mixture of heterosides at 1 mg/ml.

d) Anti-Inflammatory Activity-PMA Stress:

Given the lack of effect of IFN-γ on the production and release of PGE-2, the anti-inflammatory effect of the active agents was studied on normal human keratinocytes (strain $K_{02-1}H_6$) stimulated with PMA. Each active agent was tested at 4 concentrations:

C1=0.10 mg/ml C2=0.25 mg/ml C3=0.50 mg/ml C4=1.00 mg/ml

Assay Conditions:

1. Treatment of the cells, for 48 h, with the product being studied before induction of the irritative stress.
2. Induction of the irritative stress: PMA (10 ng/ml).
3. Incubation of the "activated" cells, for 24 h, in the presence of the product being studied.
4. Assay of PGE-2 (extracellular) and assay of cellular proteins.

Release of PGE-2

Tables 37 to 39 below group together the amounts of PGE-2 (pg/µg prot.) obtained after activation of the cells (+PMA), and also the basal amounts (—PMA). The PMA-induced production of PGE-2 and the anti-inflammatory activity (AIA) were calculated, for each concentration, according to: PGE-2 production=[(PGE-2$_{(+PMA)}$−PGE-2$_{(-PMA)}$)]

$$AIA = [(PGE\text{-}2 \text{ production}_{(control\ cells)} - PGE2 \text{ production}_{(treated\ cells)} / PGE\text{-}2 \text{ production}_{control\ cells}] \times 100$$

TABLE 38

Terminoloside

|  | Control (−PMA) | Control (+PMA) | PMA + active agent "TERMINOLOSIDE" | | | |
|---|---|---|---|---|---|---|
|  | — | 0 mg/ml | 0.1 mg/ml | 0.25 mg/ml | 0.5 mg/ml | 1 mg/ml |
| PGE-2 (pg/µg prot) | 165.8 +/− 19.8 | 660.0 +/− 51.6 | 660.0 +/− 29.9 | 606.80 +/− 63.6 | 445.7 +/− 16.7 | 321.0 +/− 21.1 |
| PGE-2 production |  | 494.2 | 494.2 | 441.0 | 279.9 | 115.2 |
| Anti-inflammatory activity (%) |  |  | 0% | 10.8% | 43.4% | 68.6% |

In the control (+PMA) batch, exposure of the keratinocytes to PMA results in a very considerable production and release of PGE-2 into the control culture media. The basal amount recorded in the nonstimulated cultures is multiplied 4-fold after stimulation with PMA, confirming that PGE-2 is a cytokine for which the expression, the production and the release can be induced with PMA. The results show a dose-dependent decrease in PGE-2 in the batches treated with terminoloside and stimulated with PMA. The differences in the batches $C_3$ and $C_4$ are statistically significant ($p \leqq 0.01$, Student's t test). The 1 mg/ml concentration is capable of reducing by 69% the release of PGE-2.

TABLE 39

| | Madecassoside | | | | |
|---|---|---|---|---|---|
| | Control (−PMA) | Control (+PMA) | PMA + MADECASSOSIDE | | |
| | — | 0 mg/ml | 0.1 mg/ml | 0.25 mg/ml | 0.5 mg/ml | 1 mg/ml |
| PGE-2 (pg/μg prot) | 165.8 +/− 19.8 | 660.0 +/− 51.6 | 622.7 +/− 18.9 | 618.1 +/− 20.7 | 436.3 +/− 32.1 | 348.3 +/− 17.8 |
| PGE-2 production | | 494.2 | 456.9 | 452.3 | 270.5 | 182.5 |
| Anti-inflammatory activity (%) | | | 7.5% | 8.5% | 45.3% | 63.1% |

A clear decrease in the amount of PGE-2 is recorded in the cultures treated with the active agent madecassoside. The inhibitory effect is dose-dependent. Only the differences in $C_3$ and in $C_4$ are statistically significant ($p \leqq 0.01$, Student's t test) relative to the (+)PMA control. The active agent madecassoside at a concentration of 1 mg/ml is capable of reducing by 63% the PMA-induced production of PGE-2.

TABLE 40

| | Heterosides | | | | |
|---|---|---|---|---|---|
| | Control (−PMA) | Control (+PMA) | PMA + HETEROSIDES | | |
| | — | 0 mg/ml | 0.1 mg/ml | 0.25 mg/ml | 0.5 mg/ml | 1 mg/ml |
| PGE-2 (pg/μg prot) | 165.8 +/− 19.8 | 660.0 +/− 51.6 | 646.5 +/− 33.8 | 515.1 +/− 48.4 | 326.8 +/− 15.5 | 142.1 +/− 6.6 |
| PGE-2 production | | 494.2 | 480.7 | 349.3 | 161.0 | 0 |
| Anti-inflammatory activity (%) | | | 2.7% | 29.3% | 67.4% | 100% |

The inhibitory effect is dose-dependent. The mixture of heteroside at a concentration of 1 mg/ml is capable of completely inhibiting the PMA-induced production of PGE-2.

e) Conclusion

The anti-inflammatory activity of the active agents terminoloside, madecassoside and heterosides was evaluated on an in vitro model through their ability to modulate the production of epidermal cytokines (IL-8, IL-1α and PGE-2) that play a key role in the steps of the inflammatory process. The study was carried out on normal human keratinocytes stimulated with interferon-γ (IFN-γ) or with PMA.

The anti-inflammatory activity of the active agents studied was assessed by measuring the amounts of:
IL-8 and IL-1α after activation with IFN-γ.
PGE-2 after stimulation with PMA.
Under the experimental conditions selected, this study showed that:
IFN-γ, within the range of concentrations tested (100 to 2000 U/ml), induces, in a dose-dependent manner, a clear stimulation of the production of IL-1α (intracellular) and brings about the production and release of IL-8 into the culture media. On the other hand, the same concentrations of IFN-γ are not capable of stimulating the release of PGE-2.
PMA, at a nontoxic dose (10 ng/ml), brings about the release of PGE-2 into the culture media.
the active agents terminoloside, madecassoside and heterosides are capable of modulating the production of the interleukins IL-8 and IL-1α, and also that of prostaglandin-2 in response to inflammatory stress. Comparison of the amounts of cytokines demonstrated anti-inflammatory effects that were variable according to the products studied, the type of cytokine under consideration and the changes observed:
with respect to IL-8

The three active agents tested are capable of modulating, in a dose-dependent manner, the production and extracellular release of this cytokine.

If the amount of cytokine recorded after treatment of the cells with the highest concentration of active agent is considered, the three products tested can be classified, according to their anti-inflammatory potential, in the following way:
heterosides>madecassoside>terminoloside
with respect to IL-1α

The three active agents tested are capable of also reducing the IFN-γ-induced production and intracellular accumulation of IL-1α. The 3 products tested can be classified, according to the maximum anti-inflammatory effect, in the following way:
terminoloside≧heterosides≧madecassoside
with respect to PGE-2

The 2 active agents, madecassoside and terminoloside, are capable of very clearly reducing the PMA-induced release of PGE-2. The mixture of heterosides is capable of completely inhibiting the PMA-induced production of PGE-2. These results make it possible to classify the products in the following way:
heterosides>madecassoside≈terminoloside Given the important role of these cytokines in the inflammatory process, the ability manifested by the active agents terminoloside, madecassoside and heterosides to substantially modulate the production of the interleukins IL-8 and IL-1α, and also that of prostaglandin-2, by keratinocytes stimulated in vitro, can be considered to be an element that is very favorable to the desired "anti-inflammatory" activity.

The invention claimed is:

1. An extract of *Centella asiatica* having more than 95 wt % of a mixture comprising madecassoside and terminoloside relative to the total weight of the extract prepared by a process comprising the steps of:
   a) creating an extract by exposing the parts of *Centella asiatica* that are above ground to an alcoholic solvent to obtain an alcoholic solution;
   b) passing the alcoholic solution obtained in step a), over an anionic resin to obtain an aqueous-alcoholic eluate;
   c) selectively defatting the aqueous-alcoholic eluate obtained in step b) by liquid/liquid extraction to obtain a defatted aqueous-alcoholic phase;
   d) concentrating the defatted aqueous-alcoholic phase obtained in step c) using successive filtration to obtain an aqueous phase;
   e) passing the aqueous phase obtained in step d), over a cationic resin and then over an anionic resin;
   f) stabilizing the aqueous phase obtained in step e) by adding alcohol to obtain a prepurified aqueous-alcoholic phase;
   g) separating the prepurified aqueous-alcoholic phase obtained in step f) using a chromatographic column having a stationary phase and a mobile phase; and
   h) obtaining a mixture comprising more than 95 wt % of madecassoside and terminoloside relative to the total weight of the extract.

2. The extract of *Centella asiatica* of claim 1, wherein the weight ratio of madecassoside to terminoloside is between 30:70 and 70:30.

3. The extract of claim 1, prepared by a process further comprising the step of: standardizing the mixture obtained in step f), by adding an appropriate amount of the extract of claim 1 so that the final extract obtained has between 90 wt % and 98 wt % of madecassoside, terminoloside and asiaticoside relative to the total weight of the final extract.

4. A standardized extract of *Centella asiatica* that comprises at least 75 wt % of a mixture of madecassoside, terminoloside and asiaticoside relative to the total weight of the final extract prepared by a process comprising the steps of:
   a) creating an extract by exposing the parts of *Centella asiatica* that are above ground to an alcoholic solvent to obtain an alcoholic solution;
   b) passing the alcoholic solution obtained in step a), over an anionic resin to obtain an aqueous-alcoholic eluate;
   c) selectively defatting the aqueous-alcoholic eluate obtained in step b) by liquid/liquid extraction to obtain a defatted aqueous-alcoholic phase;
   d) concentrating the defatted aqueous-alcoholic phase obtained in step c) using successive filtration to obtain an aqueous phase;
   e) passing the aqueous phase obtained in step d), over a cationic resin and then over an anionic resin;
   f) stabilizing the aqueous phase obtained in step e) by adding alcohol to obtain a mixture comprising madecassoside, terminoloside and asiaticoside; and
   g) standardizing the mixture obtained in step f), by adding an appropriate amount of the extract of claim 1 so that the final extract obtained has at least 75 wt % of a mixture of madecassoside, terminoloside and asiaticoside relative to the total weight of the final extract.

5. The standardized extract of claim 4, wherein the mass ratio of asiaticoside to madecassoside and terminoloside is between 5:95 and 25:75.

6. The standardized extract of claim 5, wherein the mass ratio of madecassoside to terminoloside is between 30:70 and 70:30.

7. A pharmaceutical or cosmetic composition comprising an extract of *Centella asiatica* of claim 1, and a pharmaceutically or cosmetically acceptable product.

8. A method of regulating inflammatory mechanism comprising administering the composition of claim 7 to a patient in need thereof.

9. A method of treating psoriasis, autoimmune disease, chronic inflammatory disease, and/or atopic inflammatory disease comprising administering the drug of claim 7 to a patient in need thereof.

10. A method of treating eczema and atopic dermatitis comprising administering the drug of claim 7 to a patient in need thereof.

11. A method of treating chronic inflammation associated with skin aging comprising administering the drug of claim 7 to a patient in need thereof.

12. A method of regulating dermal tissue homeostasis comprising administering the composition of claim 7 to a patient in need thereof.

13. A pharmaceutical or cosmetic composition comprising an extract of *Centella asiatica* of claim 4 and a pharmaceutically or cosmetically acceptable support.

14. The extract of *Centella asiatica* of claim 2, wherein the weight ratio of madecassoside to terminoloside is between 40:60 and 60:40.

15. A standardized extract of *Centella asiatica* that comprises at least 75 wt % of a mixture of madecassoside and terminoloside relative to the total weight of the final extract prepared by a process comprising the steps of:
   a) creating an extract by exposing the parts of *Centella asiatica* that are above ground to an alcoholic solvent to obtain an alcoholic solution;
   b) passing the alcoholic solution obtained in step a), over an anionic resin to obtain an aqueous-alcoholic eluate;
   c) selectively defatting the aqueous-alcoholic eluate obtained in step b) by liquid/liquid extraction to obtain a defatted aqueous-alcoholic phase;
   d) concentrating the defatted aqueous-alcoholic phase obtained in step c) using successive filtration to obtain an aqueous phase;
   e) passing the aqueous phase obtained in step d), over a cationic resin and then over an anionic resin;
   f) stabilizing the aqueous phase obtained in step e) by adding alcohol to obtain a prepurified aqueous-alcoholic phase;
   g) standardizing the mixture obtained in step f), by adding an appropriate amount of the extract of claim 1;
   h) separating the prepurified aqueous-alcoholic phase obtained in step g) using a chromatographic column having a stationary phase and a mobile phase; and
   i) obtaining at least 75 wt % of a mixture of madecassoside and terminoloside.

16. A standardized extract of *Centella asiatica* that comprises at least 85 wt % of a mixture of madecassoside, terminoloside and asiaticoside relative to the total weight of the final extract prepared by a process comprising the steps of:
   a) creating an extract by exposing the parts of *Centella asiatica* that are above ground to an alcoholic solvent to obtain an alcoholic solution;

b) passing the alcoholic solution obtained in step a), over an anionic resin to obtain an aqueous-alcoholic eluate;

c) selectively defatting the aqueous-alcoholic eluate obtained in step b) by liquid/liquid extraction to obtain a defatted aqueous-alcoholic phase;

d) concentrating the defatted aqueous-alcoholic phase obtained in step c) using successive filtration to obtain an aqueous phase;

e) passing the aqueous phase obtained in step d), over a cationic resin and then over an anionic resin;

f) stabilizing the aqueous phase obtained in step e) by adding alcohol to obtain a mixture comprising madecassoside, terminoloside and asiaticoside; and g) standardizing the mixture obtained in step f), by adding an appropriate amount of the extract of claim 1 so that the final extract obtained has at least 85 wt % of a mixture of madecassoside, terminoloside and asiaticoside relative to the total weight of the final extract.

17. A standardized extract of *Centella asiatica* that comprises at least 85 wt % of a mixture of madecassoside and terminoloside relative to the total weight of the final extract prepared by a process comprising the steps of:

a) creating an extract by exposing the parts of *Centella asiatica* that are above ground to an alcoholic solvent to obtain an alcoholic solution;

b) passing the alcoholic solution obtained in step a), over an anionic resin to obtain an aqueous-alcoholic eluate;

c) selectively defatting the aqueous-alcoholic eluate obtained in step b) by liquid/liquid extraction to obtain a defatted aqueous-alcoholic phase;

d) concentrating the defatted aqueous-alcoholic phase obtained in step c) using successive filtration to obtain an aqueous phase;

e) passing the aqueous phase obtained in step d), over a cationic resin and then over an anionic resin;

f) stabilizing the aqueous phase obtained in step e) by adding alcohol to obtain a prepurified aqueous-alcoholic phase;

g) standardizing the mixture obtained in step f), by adding an appropriate amount of the extract of claim 1;

h) separating the prepurified aqueous-alcoholic phase obtained in step g) using a chromatographic column having a stationary phase and a mobile phase; and i) obtaining at least 85 wt % of a mixture of madecassoside and terminoloside.

18. The standardized extract of claim 6, wherein the mass ratio of madecassoside to terminoloside is between 40:60 and 60:40.

19. An extract of *Centella asiatica* having more than 95 wt % of a mixture comprising madecassoside and terminoloside relative to the total weight of the extract.

20. A standardized extract of *Centella asiatica* that comprises 75 wt % of a mixture of madecassoside, terminoloside and asiaticoside relative to the total weight of the final extract.

21. A standardized extract of *Centella asiatica* that comprises 85 wt % of a mixture of madecassoside, terminoloside and asiaticoside relative to the total weight of the final extract.

22. A drug comprising the extract of *Centella asiatica* of claim 21 and a pharmaceutically acceptable support.

23. A method of regulating inflammatory mechanism comprising administering the drug of claim 22 to a patient in need thereof.

24. A method of treating psoriasis, autoimmune disease, chronic inflammatory disease, and/or atopic inflammatory disease comprising administering the drug of claim 22 to a patient in need thereof.

25. A method of treating eczema and atopic dermatitis comprising administering the drug of claim 22 to a patient in need thereof.

26. A method of treating chronic inflammation associated with skin aging comprising administering the drug of claim 22 to a patient in need thereof.

27. A method of regulating dermal tissue homeostasis comprising administering the drug of claim 22 to a patient in need thereof.

* * * * *

UNITED STATES PATENT AND TRADEMARK OFFICE
CERTIFICATE OF CORRECTION

PATENT NO. : 8,163,706 B2
APPLICATION NO. : 12/009696
DATED : April 24, 2012
INVENTOR(S) : Alain Loiseau, Gérard Sene and Eric Theron It is certified that error appears in the above-identified patent and that said Letters Patent is hereby corrected as shown below:

In the Claims

Column 48, line 21, Claim 22, "claim 21" should read -- claim 19 --.

Signed and Sealed this
Tenth Day of September, 2013

Teresa Stanek Rea
*Acting Director of the United States Patent and Trademark Office*